US008882660B2

(12) United States Patent
Phee et al.

(10) Patent No.: US 8,882,660 B2
(45) Date of Patent: Nov. 11, 2014

(54) ROBOTIC SYSTEM FOR FLEXIBLE ENDOSCOPY

(75) Inventors: Soo Jay Louis Phee, Singapore (SG); Soon Chiang Low, Singapore (SG); Khek Yu Ho, Singapore (SG); Sheung Chee Chung, Hong Kong (CN)

(73) Assignees: Nanyang Technological University, Singapore (SG); National University of Singapore, Singapore (SG)

( * ) Notice: Subject to any disclaimer, the term of this patent is extended or adjusted under 35 U.S.C. 154(b) by 61 days.

(21) Appl. No.: 13/322,879

(22) PCT Filed: May 31, 2010

(86) PCT No.: PCT/SG2010/000200
§ 371 (c)(1),
(2), (4) Date: Nov. 28, 2011

(87) PCT Pub. No.: WO2010/138083
PCT Pub. Date: Dec. 2, 2010

(65) Prior Publication Data
US 2012/0078053 A1    Mar. 29, 2012

Related U.S. Application Data

(60) Provisional application No. 61/182,556, filed on May 29, 2009.

(51) Int. Cl.
| | | |
|---|---|---|
| A61B 1/00 | (2006.01) | |
| A61B 19/00 | (2006.01) | |
| A61B 18/14 | (2006.01) | |
| A61B 17/29 | (2006.01) | |
| A61B 17/00 | (2006.01) | |

(52) U.S. Cl.
CPC ....... A61B 19/2203 (2013.01); *A61B 2019/464* (2013.01); *A61B 2019/2211* (2013.01); *A61B 18/14* (2013.01); *A61B 2018/1495* (2013.01); A61B 1/00147 (2013.01); *A61B 2018/1422* (2013.01); *A61B 2017/2929* (2013.01); *A61B 2017/2906* (2013.01); *A61B 2017/00278* (2013.01); *A61B 2017/00292* (2013.01); *A61B 2017/00296* (2013.01); *A61B 2019/2223* (2013.01); *A61B 2019/2296* (2013.01); *Y10S 901/34* (2013.01)
USPC .............. 600/139; 901/34; 606/130

(58) Field of Classification Search
USPC ............... 600/139; 318/568.21; 901/2, 34; 74/490.01; 700/254; 606/130
See application file for complete search history.

(56) References Cited

U.S. PATENT DOCUMENTS

| | | | |
|---|---|---|---|
| 4,967,126 A | 10/1990 | Gretz et al. | |
| 5,546,508 A | 8/1996 | Jain et al. | |
| 5,624,398 A | 4/1997 | Smith et al. | |
| 6,692,485 B1 | 2/2004 | Brock et al. | |
| 7,090,683 B2 | 8/2006 | Brock et al. | |
| 2002/0087166 A1 | 7/2002 | Brock et al. | |
| 2006/0178556 A1 | 8/2006 | Hasser et al. | |
| 2007/0287992 A1 | 12/2007 | Diolaiti et al. | |
| 2008/0065105 A1 | 3/2008 | Larkin et al. | |
| 2008/0071291 A1* | 3/2008 | Duval et al. .................. | 606/130 |
| 2008/0218770 A1* | 9/2008 | Moll et al. .................... | 356/614 |

FOREIGN PATENT DOCUMENTS

WO    2007/111571    10/2007

OTHER PUBLICATIONS

Low et al., "Master-Slave Robotic System for Therapeutic Gastrointestinal Endoscopic Procedures", Proceedings of the 28th IEEE EMBS Annual International Conference, (2006), pp. 3850-3853.*
PCT International Search Report issued for PCT Application No. PCT/SG2010/000200 filed May 31, 2010 in the name of Nanyang Technological University et al.
PCT Written Opinion issued for PCT Application No. PCT/SG2010/000200 filed May 31, 2010 in the name of Nanyang Technological University et al.
PCT International Preliminary Report on Patentability issued for PCT Application No. PCT/SG2010/000200 filed May 31, 2010 in the name of Nanyang Technological University et al.
Chiang SL, et al. Kinematic and compliance analysis for tendon-driven robotic mechanisms with flexible tendons, Mechanism and Machine Theory 2005, 40: 728-739.

* cited by examiner

*Primary Examiner* — Alireza Nia
*Assistant Examiner* — Timothy J Neal
(74) *Attorney, Agent, or Firm* — Steinfl & Bruno LLP

(57) ABSTRACT

A robotic manipulator controller and system for use in flexible endoscopy, the manipulator comprising a flexible member configured to be coupled to an endoscope, and an arm connected to and movable by the flexible member, wherein the flexible member has a first end connected to the arm and a second end connectable to the controller to allow a physical movement of the arm to be controllable by a physical movement of the controller.

13 Claims, 14 Drawing Sheets

The three phases of recorded housing force

The corresponding three phases of the recorded end effector force

ROBOTIC SYSTEM FOR FLEXIBLE ENDOSCOPY

CROSS REFERENCE TO RELATED APPLICATIONS

The present application is the US national stage of International Application PCT/SG2010/000200 filed on May 31, 2010 which, in turn, claims priority to U.S. Provisional Application 61/182,556 filed on May 29, 2009.

FIELD OF THE INVENTION

The present invention relates to a robotic system for flexible endoscopy and in particular but not exclusively to robotic manipulators, controllers, systems, methods and uses thereof for performing surgery.

BACKGROUND OF THE INVENTION

In line with minimally invasive surgery (MIS), flexible endoscopy is used to inspect and treat disorders of the gastrointestinal (GI) tract without the need for creating an artificial opening on the patient's body. The endoscope is introduced via the mouth or anus into the upper or lower GI tracts respectively. A miniature camera at the distal end captures images of the GI wall that help the clinician in his/her diagnosis of the GI diseases. Simple surgical procedures (like polypectomy and biopsy) can be performed by introducing a flexible tool via a working channel to reach the site of interest at the distal end. The types of procedures that can be performed in this manner are limited by the lack of manoeuvrability of the tool. More technically demanding surgical procedures like hemostasis for arterial bleeding, suturing to mend a perforation, fundoplication for gastrooesophageal reflux cannot be effectively achieved with flexible endoscopy. These procedures are often presently being performed under open or laparoscopic surgeries.

Endoscopic submucosal dissection (ESD) is mostly performed using standard endoscope with endoscopically deployed knifes. Performing ESD thus requires tremendous amounts of skill on the part of the endoscopist and takes much time to complete. Furthermore, constraint in instrumental control makes it prone to procedural complications such as delayed bleeding, significant bleeding, perforation, and surgical procedural complications. Although ESD is increasingly recognized as an effective procedure for the treatment of early-stage gastric cancers, due to these problems, ESD remains a procedure performed only by the most skilled endoscopists or surgeons. Severe limitations in the manoeuvring of multiple instruments within the gastric lumen pose a major challenge to the endoluminal operation. Natural force transmission from the operator is also hampered by the sheer length of the endoscope, resulting in diminished, and often, insufficient force at the effector end for effectual manipulations. Besides, as all instruments are deployed in line with the axis of the endoscope, off-axis motions (e.g. triangulation of the instruments) are rendered impossible.

Natural Orifices Transluminal Endoscopic Surgery (NOTES), a surgery using the mouth, anus, vaginal, nose to gain entry into the body) is a method used for surgery that does not require any percutaneous incisions on the abdominal wall. However, for NOTES to be used on human safely, many technical issues need to be addressed. Out of which tooling for fast and safe access and closure of abdominal cavity and spatial orientation during operation are of paramount importance.

With the invention of medical robots like the Da Vinci surgical systems, clinicians are now able to manoeuvre surgical tools accurately and easily within the human body. Operating from a master console, the clinician is able to control the movements of laparoscopic surgical tools real time. These tools are commonly known as slaves. However, master-slave surgical robotic systems are rigid and the slave manipulators enter the human body by means of incisions.

Diseases of the GI tract such as, for example, peptic ulcer, gastric cancer, colorectal neoplasms, and so forth, are common in most countries. These conditions can be diagnosed with the aid of the flexible endoscopes. Endoscopes incorporate advanced video, computer, material, and engineering technologies. However, endoscopists often still complain of the technical difficulties involved in introducing long, flexible shafts into the patient's anus or mouth and there is still a tool lacking to carry out GI surgeries without creating an incision in the human body and over as short a time as possible since time is an essence during acute GI bleeding.

SUMMARY OF THE INVENTION

The present invention is defined in the appended independent claims. Some optional features of the present invention are defined in the appended dependent claims.

According to a first aspect, the present invention relates to a robotic manipulator for flexible endoscopy comprising:
  a flexible member configured to be coupled to an endoscope, and
  an arm connected to and movable by the flexible member, wherein the flexible member has a first end connected to the arm and a second end connectable to a controller to allow a physical movement of the arm to be controllable by a physical movement of the controller.

The robotic manipulator may be used to perform intricate and precise surgical intervention. It may be inserted into the tool channel of existing endoscopes or attached in tandem to the endoscope. The robotic manipulator may allow for real time endoscopic view, thus providing the advantage to the endoscopist for performing more intricate and difficult surgical procedures using natural orifices to access the internal organs. In particular, the GI tract thus eliminating any scars on the patient.

In various embodiments, the robotic manipulators may be attached to the endoscope and introduced into the patient together. In other exemplary embodiments, the endoscope may be introduced first into the patient with the manipulators being introduced after the site of interest has been reached. In various exemplary embodiments, hollow, flexible tubes can be attached to the endoscope, and manipulators can be threaded through these tubes to reach the distal end. The endoscope also provides tool channels for instruments to go through which enable the endoscopist to perform a variety of treatments such as biopsy, polypectomy, marking, haemostasis, etc. Some endoscopes have two tool channels that can potentially accommodate two robotic arms. Alternatively, endoscopes may be custom designed to accommodate the robotic manipulator. Accordingly, the term "coupled to" in relation to the interrelationship between the flexible member and the endoscope covers fixed attachments, removable attachments, or even simple contacting or supporting dispositions.

The endoscope may be used to inspect, diagnose and treat various pathologies in the upper or lower GI tract. A typical endoscope includes an ultra compact Charged-Coupled Device (CCD) camera, light source and a channel for infusing or withdrawing liquid or gas from the patient's body. The tip of the endoscope may also be steerable so that the endoscope may be able to transverse through the winding channel of the GI tract faster, safer and giving less pain to the patient.

The provision of the flexible member that forms part of the robotic manipulator may enable the robotic manipulator to be introduced in tandem with a flexible endoscope via natural orifices (e.g. mouth and anus) to access the GI tract to perform dexterous procedures allowing the mode of power transmission to take the form of being long, narrow and flexible.

The flexible member, which transmits the torque from an actuator at the controller end to the robotic manipulator, may be a cable system. There are two types of cable system: pulley system for cable routing and tendon-sheath system.

The tendon-sheath system generally comprises of a hollow helical coil wire acting as a sheath and a cable within that acts as the tendon. When the tendon is pulled at one end, it slides within the sheath thereby allowing the pulling force to be transmitted to the other end of the sheath. The tendon in a sheath may be small enough to go through the tool channels of the endoscope and being small allows it to be easily handled. The difference between cable routing and tendon-sheath actuation is illustrated in FIG. 2. As compared to cable routing used in many robots such as Utah/MIT hand and CT arms where a pulley and a planned route for the tendon to go are required, the tendon-sheath actuation has an advantage when there are unpredictable bends inside the human GI tract. Other advantages of tendon-sheath actuation are flexibility and biocompatibility as compared to cable routing. For these reasons, the tendon sheath actuation may be selected as the flexible member for power transmission.

The size of the robotic manipulator provides the advantage of it being used with commercially available Guardus overtube and the like to access the GI tract of the animal or human body. This makes it easier, safer and more comfortable for the robotic manipulator to be introduced and removed from the animal or human patient. In particular, the tendon may be Spectra® (Ultra-High Molecular Weight Polyethylene (UH-MWPE)) fibres and sheath may be a helical metal coil. The Spectra® fibre may be bent without kinking as shown in FIG. 3 thus reducing undesirable effects such as stick and slip and sudden jerking motions at the ends of the robotic manipulator in the human/animal body. The helical metal coil provides the benefit of resisting compression, not collapsing onto the tendon, reducing friction within the robotic manipulator and thus reducing the amount of heat produced and the wear and tear of the robotic manipulator.

The tendon and sheath may be surrounded by an overtube which protects the oesophagus from unintentional scratching by the robotic manipulator. The overtube may be flexible for all the sheaths. Due to the size of the overtube and the combined stiffness of the sheath within, it may restrain the buckling of the sheaths for better performance of the surgery. Although tendon-sheath actuation is preferred, other forms of actuation may be used such as, for example, signal cables to actuators at the distal end, and so forth. Variations may depend on the procedure required. For a simple procedure, one arm may be sufficient.

The arm may be configured to have a degree of freedom allowing forward and backward motion of the arm substantially parallel to the longitudinal axis of the endoscope. This allows for the arm to work on the flesh in front of the endoscope without the endoscope having to be in contact with the flesh. Due to this motion, the endoscopist only needs to show the view of the site where the robotic manipulator needs to operate and does not have to adjust the distance from the site. The robotic manipulator may also open and close itself in order to provide triangulation during the procedure as well as reducing its size when the robotic manipulator is introduced into the human body to reduce the discomfort experienced by the patient.

The arm may comprise at least four degrees of freedom. This may resemble the human wrist bending and rotation movement thus enabling easy emulating of the physical movement at the controller end onto the arm of the robotic manipulator when performing the procedure. A high number of degrees of freedom on the arm may be necessary to be able to perform complicated procedures. The arm may be designed after a simplified human arm to be as intuitive to control as possible. The arm may comprise 2 or 3 degrees of freedom depending on the complexity of the surgery being performed.

Each degree of freedom may be controllable by two antagonistic tendons of the flexible member. In particular, each antagonistic tendon may be independently attachable to a motor at the controller. This design may benefit the robotic manipulator, as the amount of rotation of each degree of freedom may only be dependent on its own tendon and not dependent on the movement from the other degrees of freedom thus preventing unnecessary and unintentional movements of the arm. The rotational displacement of each joint of the arm may be directly proportional to the linear displacements of the tendon. This allows the robotic manipulator to be controlled easily.

The number of degrees of freedom of each arm may be equal to the number of degrees of freedom at the controller. Due to the similarity between the degrees of freedom of the controller and the arm, the user can easily visualize the control of the controller that maps to the movement of the arm. This may allow the user to use the robotic manipulator for a prolonged period of time without feeling tired.

In one embodiment, the robotic manipulator may comprise two arms. The arms may be bundled up closely together with the endoscope. For effective manipulation, the arms may spread themselves out first before moving in to the targeted area to perform the operation. Therefore, the arms may be at least two limb lengths to prevent collision between the two arms and prevent blocking of vision from the endoscope.

The arms may have end effectors in the form of monopolar or bipolar electrodes to carry out procedures involving cautery. However, because different surgical procedures require different tools, the end effectors are interchangeable. The arm may have an end effector selected from the group consisting of a gripper, hook, monopolar electrocautery hook, pincer, forceps or knife. The two arms may be used to perform different actions such as pulling and cutting of polyps or potentially suturing on the walls of the bleeding sites. For example, the endoscopist may confidently use one of the end effectors to pinch onto the GI wall while the other holds onto a needle to perform suturing. The vision provided by the endoscope may be similar to a first person view on the surrounding and the two arms may resemble the two human arms of the surgeon. This gives the impression to the surgeon that he is operating inside the patient body with his two hands allowing the surgery to be more accurate and precise.

In particular, the end effector of one arm may be in the form of a gripper, and the arm has a first joint providing a degree of freedom for controlling the opening and closing of the jaws of the gripper. More in particular, the first joint may provide a further degree of freedom for controlling the flexion or hyperextension of the gripper. Even more in particular, the arm may include a second joint providing a degree of freedom for controlling the supination or pronation of the arm. The supination/pronation joint makes it easier for the robotic manipulator to orientate itself to perform the intended procedures.

The arm may include a third joint providing a degree of freedom for controlling the opening and closing of the arm, the opening of the arm being a movement out of alignment with the longitudinal axis of the endoscope, and the closing of the arm being a movement to bring the arm into alignment with the longitudinal axis of the endoscope. These degrees of freedoms allow the robotic manipulator to have triangulation by making the arms spread out from the base with the opening and closing joint before the tip of the manipulator closes in with the flexion/hyperextension joint. In this manner, the arms of the robotic manipulator do not block the endoscopic view excessively so that the operation environment could be clearly viewed by the surgeon. These degrees of freedoms also allow the robotic manipulator to be straightened be become relatively less obstructive when it is being inserted into the patient.

The other two translation joints of the two arms are able to slide along a semi-circular cap attached to the endoscope. These two translation joints may be non-motorized joints which are controlled manually, like conventional endoscopic tools. These translation actions are manipulated by the pushing or pulling actions of the endoscopist intra-operatively. Once all the sheaths on the gripper side are pushed, the gripper may be able to be pushed further out to grab onto tissue. On the other hand, when pulling onto tissue, it creates a tension on the grasped tissue for easy cutting with the cautery hook, for example.

The end effector of another arm may be in the form of a cauterizing hook. In particular, the arm may include a first joint providing a degree of freedom for controlling the flexion or hyperextension of the cauterizing hook, a second joint providing a degree of freedom for controlling the supination or pronation of the arm, and a third joint providing a degree of freedom for controlling the opening and closing of the arm, the opening of the arm being a movement out of alignment with the longitudinal axis of the endoscope, and the closing of the arm being a movement to bring the arm into alignment with the longitudinal axis of the endoscope.

The robotic manipulator may comprise two arms comprising joints with nine degrees of freedom, wherein the first arm has an end effector in the form of a cauterizing hook and the second arm has an end effector in the form of a gripper.

The arm and/or the end effector may comprise a biosensor or a force sensor or haptics figured to provide a signal to the controller. In particular, the force sensor may be used to give the endoscopist tactile sensations during the operation. The biosensors may enable the endoscopist to know the pH or the presence of certain chemicals at the operating site. This will allow the endoscopist to vary the surgery to suit the results of the sensors.

The elongation and force at the end effector may be predicted by an end effector force prediction unit at the controller. The force prediction unit may comprise
- a receiver capable of receiving information from the end effector wherein the information allows measurement/ determination of specific parameters related to the elongation and force at the effector end;
- a processor capable of analysing the parameters to determine the specific equation between the force applied at the controller and the elongation and force applied at the end effector; and
- a module capable of implementing the equation at the controller to predict the force applied at the end effector of the robotic manipulator.

This force feedback could be used to rely useful information about the procedure back to the surgeon. A method of force prediction of the tendon sheath mechanism utilising theoretical modeling of the characteristic of the tendon sheath mechanism to predict the distal force and elongation during the various phases of the actuation may be used at the force prediction unit. This force prediciton method removes the need for sophisticated sensors at the end effectors for the robotic manipulators that have to be sterilised before use thus simplifying the procedure and maintaining the size of the robotic manipulator. This force prediction method requires a set of external sensors located at the actuator at the controller end. The output reading of the sensors may be used to predict the force experienced by the end effectors. The result of the force prediction is used as the input for the actuator at the controller end in order to provide force feedback to the surgeon.

Therefore by using this force prediction method, the surgeon is able feel the force that the robotic manipulators are exerting on the surroundings. This ensures the surgeon does not cause unnecessary trauma to the patient's body and also ensures that the robotic manipulator or the system does not break down due to excessive tension on the tendon. The surgery may then be carried out faster, safer and in a more consistent manner.

According to another aspect, the present invention provides a controller for controlling the movements of a robotic manipulator for flexible endoscopy comprising:
- a hand-held member configured for use by a user to effect movements of the robotic manipulator, wherein the hand-held member comprises joints providing degrees of freedom corresponding to the degrees of freedom of the robotic manipulator.

The controller may be able to generate movements above the level of the user's detection and may provide significant information from the robotic manipulator to the user. The controller may also possess higher position resolution than the robotic manipulator. Its friction, mass and inertia may be low enough to give comfort to the user.

The controller may include a microprocessor configured to:
- detect the motions of the hand-held member,
- scale the motion detected to suit the robotic manipulator, and
- transmit signals to an actuator for controlling flexible members connected to the robotic manipulator.

The microprocessor may also be a motion controller. In one exemplary embodiment, it is a console and is essentially the 'brain' of the system. It reads information from the controller. Software calculates the required kinematics of the robotic manipulator. Output signals are then sent to the motion controller to actuate the motors and other prime movers accordingly. Input signals from the robot manipulator's sensors are also constantly being read by the microprocessor to ensure that the former is moving in the required manner. Other functions of this microprocessor include scaling down of the clinician's movements. Ideally, the robotic manipulator should move by significantly less that the movement of the clinician movement for accuracy and safety.

The controller may comprise multiple rotary encoders that read the values of the movement the user makes and feeds it to the microprocessor for analysis and subsequently control of the robotic manipulator.

The hand-held member may include a prime mover to receive signals from the robotic manipulator and to provide feedback to a user using the hand-held member. This allows the user to feel a sensation when the robotic manipulator exerts a force on the environment during the operation. This makes the operation safer and faster due to the additional information.

The microprocessor may comprise a computer that does the mapping between the readings of the controller as well as electronic housing that has all the relevant wirings for the system to work. The microprocessor reads in the sensors reading from the rotary encoders of the controller and then uses a software program that scales and actuates the amount of movement of the various prime movers at the actuator.

The microprocessor may comprise an electronics housing to hold all the relevant circuitries of the system such as amplifiers and power supplies and protect them from the outside elements and ensures the wiring within is not disturbed during transportation to prevent any wiring errors to the system.

The actuator may be designed to be easily portable as well as a compact size.

The hand-held member may comprise grippers attachable to fingers of the user. In particular, the robotic manipulator may be controllable using the grippers. That means the user can rest his/her elbow, improving the comfort and user-friendliness of the controller. The controller may further comprise an armrest configured to receive a user's arm for providing greater comfort.

The hand-held member may comprise a plurality of linkages that may be adjustable to suit different users. The size of the linkages may be small so that the weight of the controller may be reduced. Counter-weight mechanisms may be put in place to ensure that the user feels very little weight when operating the controller. Also, the non-wearing characteristic of the controller eliminates the weight of linkages that would help the surgeon control the controller effectively when the operation is carried out for a long time. This reduces user fatigue. The length of the base of the gripper linkage may be adjustable. This makes it possible for motion scaling mechanically, if necessary. Vision intrusion may also be reduced with simpler and fewer linkages.

Two different-colour pedals at the base of the controller may be present to control the cauterization and coagulation mode of the hook. While focusing on the task and being busy with the controller on hand, it may be more convenient for the surgeon to control the cutting action by stepping onto the pedals with his foot.

According to another aspect, the present invention provides a robotic system for flexible endoscopy comprising a robotic manipulator according to any aspect of the present invention and a controller according to any aspect of the present invention.

According to a further aspect, the present invention provides a method of flexible endoscopy comprising the step of inserting the robotic manipulator according to any aspect of the present invention into a natural orifice of the human body.

According to one aspect, the present invention provides a method of treatment of a gastrointerinal tract related disease comprising the step of inserting the robotic manipulator according to any aspect of the preset invention into a natural orifice of the human body.

According to another aspect, the present invention provides a use of a robotic system according to any aspect of the present invention for the treatment of a gastrointerinal tract related disease.

According to yet another aspect, the present invention provides a method of predicting the force and elongation at the end of a robotic manipulator, comprising the steps of:
(a) receiving information from the end of the robotic manipulator, wherein the information allows measurement/determination of specific parameters related to the elongation and force at the end of the robotic manipulator,
(b) analysing the parameters to determine the specific equation between the force applied at a controller and the elongation and force applied at the end of the robotic manipulator; and
(c) implementing the equation at the controller to predict the force applied at the end effector of the robotic manipulator This method may be used for predicting the end effector parameters for any robotic arm having relatively constant sheath shapes. This offers an additional advantage of locating the sensors away from the end effector. This reduces the inertia of the end effector and allows the robotic manipulator to work in extreme environmental conditions, whereby sensors at the end effector would fail.

As will be apparent from the following description, preferred embodiments of the present invention allow an optimal use of both robotic manipulator operations and controller operations to take advantage of the manoeuvrability and size of these components in flexible endoscopy to carry out dextrous GI related procedures more efficiently and accurately. This and other related advantages will be apparent to skilled persons from the description below.

BRIEF DESCRIPTION OF THE FIGURES

Preferred embodiments of the invention will now be described by way of example only with reference to the following figures.

DETAILED DESCRIPTION OF THE PREFERRED EMBODIMENTS

Figure 1:
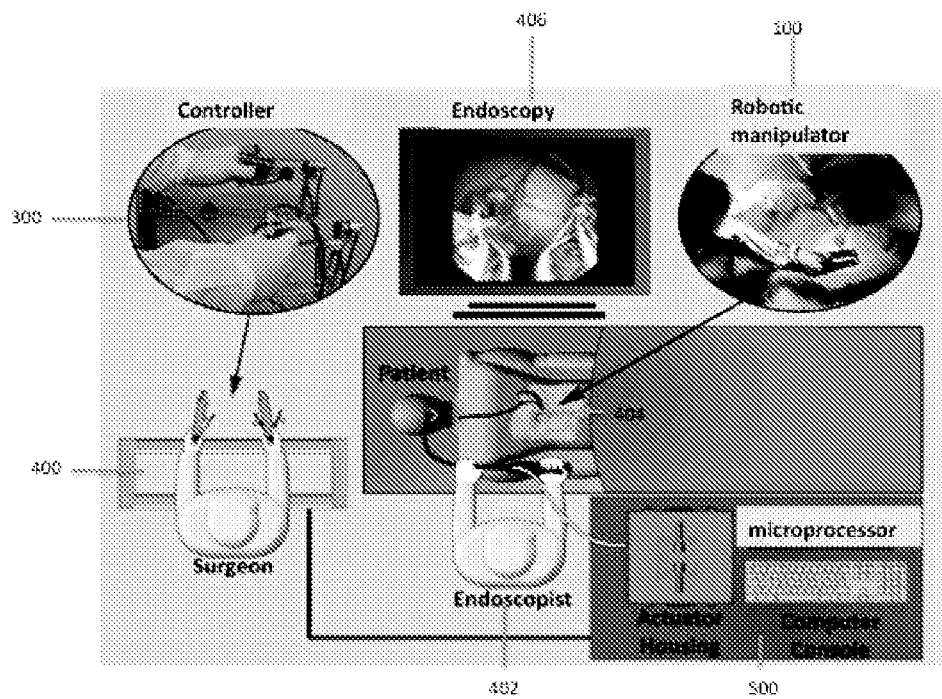
FIG. 1 is a schematic layout of the exemplary embodiment of the robotic system (Master And Slave Transluminal Endoscopic Robot; MASTER)
Figure 2:
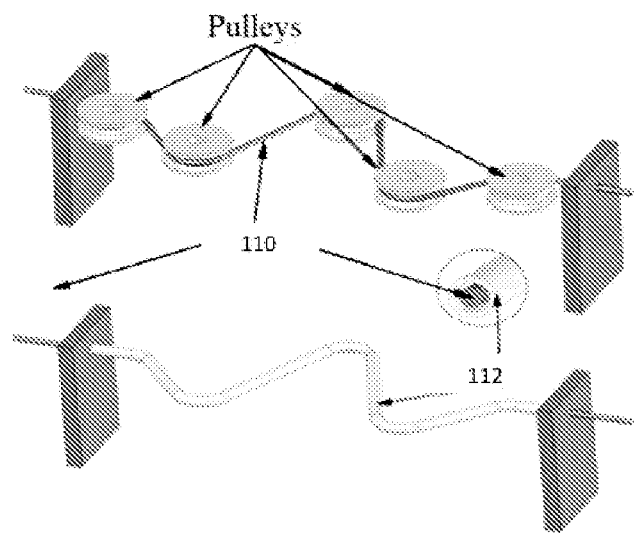
FIG. 2 is a diagram showing the difference between cable routing and tendon-sheath actuation.
Figure 3:
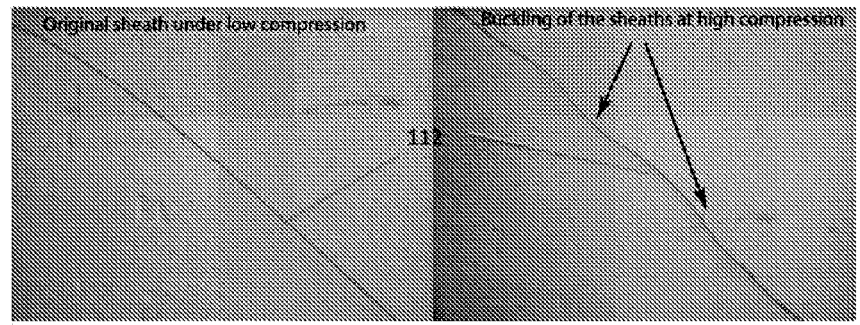
FIG. 3 is an image showing the buckling of the sheath.

In the exemplary embodiment shown in FIG. 1, the robotic system comprises a controller 300 able to be operated by an endoscopist 402 optionally with the help of an assistant 400. The robotic system also has a microprocessor 500 connected to the controller 300 to control movements of a robotic manipulator 100 on a patient 404. The system further comprises a conventional endoscopy system 406.

The robotic manipulator 100 comprises a flexible member (a tendon in sheath in the preferred embodiment) configured to be coupled to an endoscope, and an arm connected to and movable by the flexible member. As will be detailed below, the flexible member has a first end connected to the arm and a second end connectable to a controller to allow a physical movement of the arm to be controllable by a physical movement of the controller.

Figure 4A:
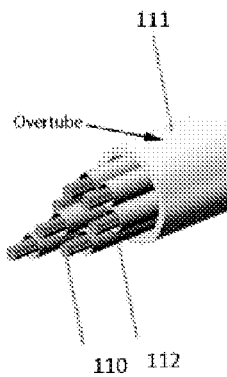
FIG. 4A is a diagram showing the overtube with the loaded sheaths.
Figure 4B:
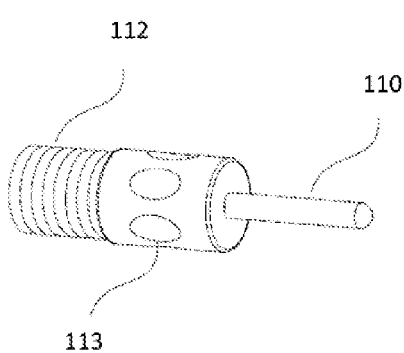
FIG. 4B illustrates a tendon within a helical metal coil.

FIG. 4A shows an exemplary embodiment of a plurality of tendons 110 in sheaths 112 as a flexible member. To allow the endoscope 406 and the robotic system to be inserted with ease, an overtube 111 may be first inserted through the oesophagus. The overtube 111 tightly constrains the sheaths 112 and prevents buckling. The overtube 111 itself is still highly flexible for the application of surgical robot. FIG. 4B shows a tendon 110 within a sheath 112 implemented as a helical metal coil.

Figure 5A:
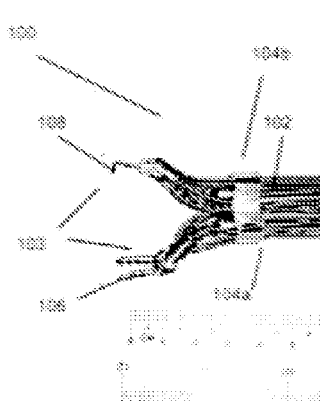
FIGS. 5A and 5B are views of the exemplary embodiment robotic manipulator showing the size of the robotic manipulator.

FIGS. 5A and B shows an exemplary embodiment of the robotic manipulator 100. The robotic manipulator 100 is able to operate with the required number of degrees of freedom (DOFs) to accurately replicate the hand and wrist motions of the endoscopist 402 within the GI tract in real time. The robotic manipulator 100 includes a flexible member 102 configured to be coupled to an endoscope 406 with a first end (that enters the patient) of the flexible member connected to an arm 104a, 104b and the second end connectable to a controller (not shown). In order to avoid interference with the operation of the endoscopist, the length of the flexible member 102 is 2 m, which is 0.5 m longer than the endoscope. The exemplary embodiment of the robotic manipulator 100 has two arms 104a, 104b. One end of the arms is attached to the flexible member 102 and the other end of the arms is attached to an end effector 103. The arm 104a is attached at one end to an end effector 103 in the form of a gripper 106. The arm 104b is attached at one end to an end effector 103 in the form of a hook 108.

Figure 5B:
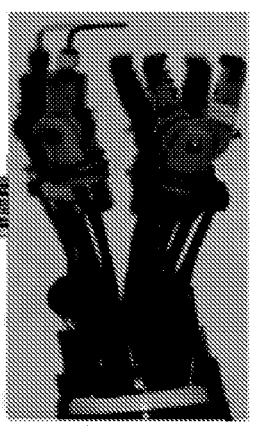
Figure 5C:
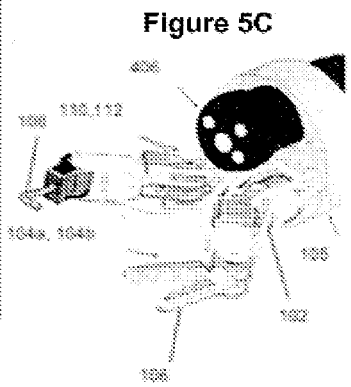
FIG. 5C is a perspective view of the exemplary embodiment robotic manipulator attached to an endoscope.

FIG. 5C shows an exemplary embodiment of the robotic manipulator 100 coupled to an endoscope 406. As noted earlier, the flexible member 102 comprises a plurality of tendons 110 in sheaths 112.

The endoscope 406 has a tool channel (not shown) into which the flexible member 102 can be inserted to drive a robotic manipulator 100 with effector ends 103. The endoscope 406 is inserted by the endoscopist 402 who can observe progress on a monitor (not shown). When the endoscope 406 has traversed to the area of interest within the GI tract, the robotic manipulator 100 is inserted by the clinician 402 until the end effectors 103 appear at the distal end of the endoscope 406. The clinician 402 then moves to the controller 300 where he uses his fingers to control an ergonomically designed mechanical controller 300 as is described below. The entire robotic manipulator 100 is designed to be small, slender and flexible enough to be threaded through the tool channels of a dual-channel therapeutic endoscope 406 (GIF-2T160, Olympus Medical Systems Corporation, Japan), which is connected to a standard endoscope image system (EVIS EXERA II Universal Platform, Olympus Medical Systems Corporation, Japan).

Ideally, the system would be operated by an endoscopist and a surgeon. The former would traverse and manoeuvre the endoscope while the latter would sit in front of the controller to control the robotic manipulators.

The exemplary embodiment robotic manipulator 100 illustrated has nine degrees of freedom (indicated with arrows in FIG. 6) and is anthropomorphic to the human arm (elbow to wrist). A robotic manipulator 100 with two arms 104a, 104b attach to the distal end of a conventional flexible endoscope 406 using an attachment 105 that couples to the distal end and supports the arms 104a, 104b. The arms 104a, 104b together with the end effectors 103 are actuated by flexible members 102 connected to motors (not shown) at the proximal ends (i.e. ends connected to an actuator).

In order to actuate one degree of freedom, two sets of tendons 110 and sheaths 112 which work antagonistically are required for a joint to move bidirectionally. Two tendon 110 and two sheath 112 cables control one motorized degree of freedom of the robotic manipulator. At both proximal and distal ends, the sheath 112 will be stopped at the counter bore hole of the base of each degree of freedom while the tendon 110 is slid through that counter-bore hole and a tiny hole on the pulley or the rotational body. To control one degree of freedom, two tendons 110 have to be clamped at the pulley side of the robotic manipulator with wire fittings.

Figure 7:
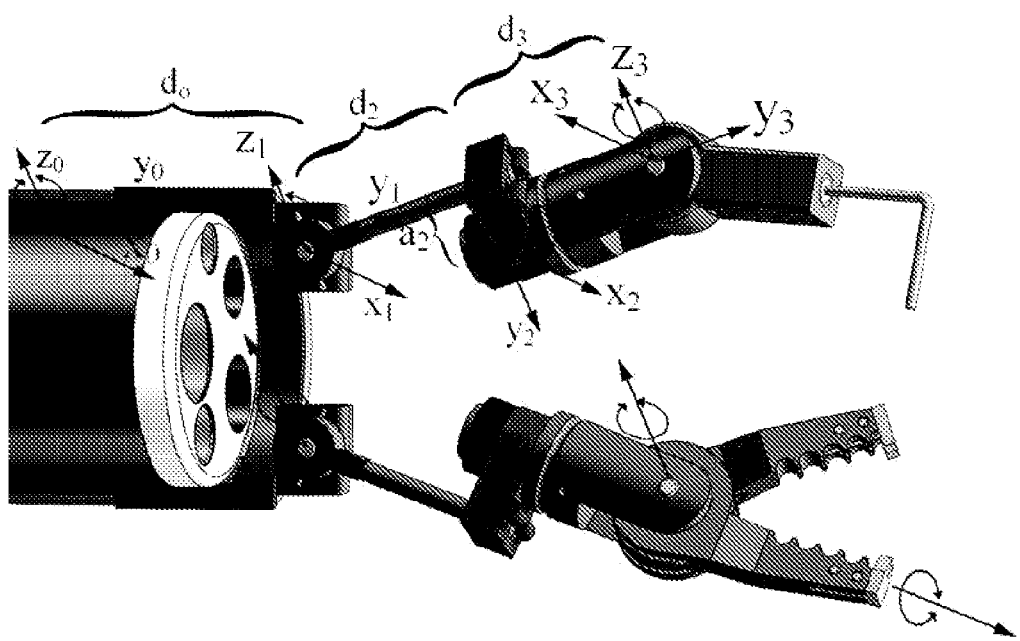
FIG. 7 is a perspective view of the robotic manipulator pointing out the joints and the parameters of each joint.

The kinematics of the robotic manipulator is represented by the Denavit-Hartenberg (DH) parameters which joint configuration and parameters of each joint are depicted in FIG. 7, and Table 1, respectively. In addition, the resultant homogeneous transformation matrix is as follow where $c\theta_i = \cos(\theta_i)$, $s\theta_i = \sin(\theta_i)$.

$$T := \begin{bmatrix} (-s\theta1\,s\theta2 + c\theta1\,c\theta2)c\theta3 & -c\theta1\,s\theta2 - s\theta1\,c\theta2 & (-s\theta1\,s\theta2 + c\theta1\,c\theta2)s\theta3 & (-c\theta1\,s\theta2 - s\theta1\,c\theta2)d3 + c\theta1\,a2c\theta2 - s\theta1\,a2s\theta2 \\ (s\theta1\,c\theta2 + c\theta1\,s\theta2)c\theta3 & -s\theta1\,s\theta2 + c\theta1\,c\theta2 & (s\theta1\,c\theta2 + c\theta1\,s\theta2)s\theta3 & (-s\theta1\,s\theta2 + c\theta1\,c\theta2)d3 + s\theta1\,a2c\theta2 + c\theta1\,a2s\theta2 \\ -s\theta3 & 0 & c\theta3 & d2 + d0 \\ 0 & 0 & 0 & 1 \end{bmatrix}$$

Figure 10:
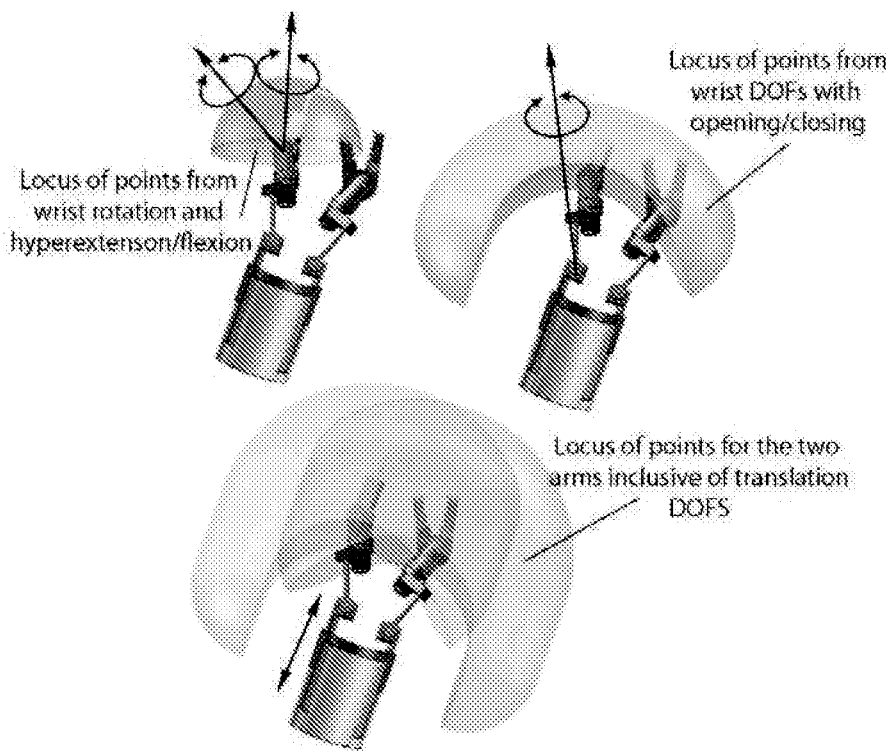
FIG. 10 is a diagram showing the workspace of the exemplary embodiment robotic manipulator.

Based on the calculated DH parameter matrix, the parameters of each link and joint, the workspace formed by the two arms of the robotic manipulator is depicted in FIG. 10. The grey spaces are the workspace of the tip of each manipulator. With such design, the robot could perform a variety of complex tasks with minimal blockage to the endoscopic camera view.

The design of the controller (as explained below) is anthropomorphic and replicates the degrees of freedom of the robotic manipulator. However, the achievable workspace for the whole system depends on the range of human arm motion as represented in Table 2. The workspace is formed using the motion range of movement of the joint from −90° to 90° although the robotic manipulator can move beyond this range.

TABLE 1

DH Parameters of robotic manipulator

| Joint (i) | θ(i) | A(i − 1) | a(i − 1) | d(i) |
|---|---|---|---|---|
| 1 | 0 | 0 | 0 | d0 |
| 2 | θ1 | 0 | 0 | 0 |
| 3 | θ2 | −90 | a2 | d2 |
| 4 | θ3 | 90 | 0 | d3 |

TABLE 2

Allowable range of motion of the controller and robotic Manipulator

| | | Range | |
|---|---|---|---|
| No: | Motion | Robotic Manipulator | Controller |
| 1 | Translation | 15 mm | |
| 2 | Opening/Closing | −45° to 90° | −45° to 45° |
| 3 | Supination/Pronation | −90° to 90° | −90° to 90° |
| 4 | Flexion/Extension | −90° to 90° | −90° to 90° |

The force that the joint exerts on the end effectors is measured and summarized in Table 3. The maximum grasping force at the flexion/extension joint is approximately 5.20 N, which is sufficient to hold and grasp onto the slippery and viscoelastic tissue during the procedure.

TABLE 3

The force exerted of the end effector's joint

| Joint Name | Force(N) |
|---|---|
| Opening/Closing | 2.87 |
| Supination/Pronation | 3.29 |
| Flexion/Extension | 5.20 |

Figure 6:
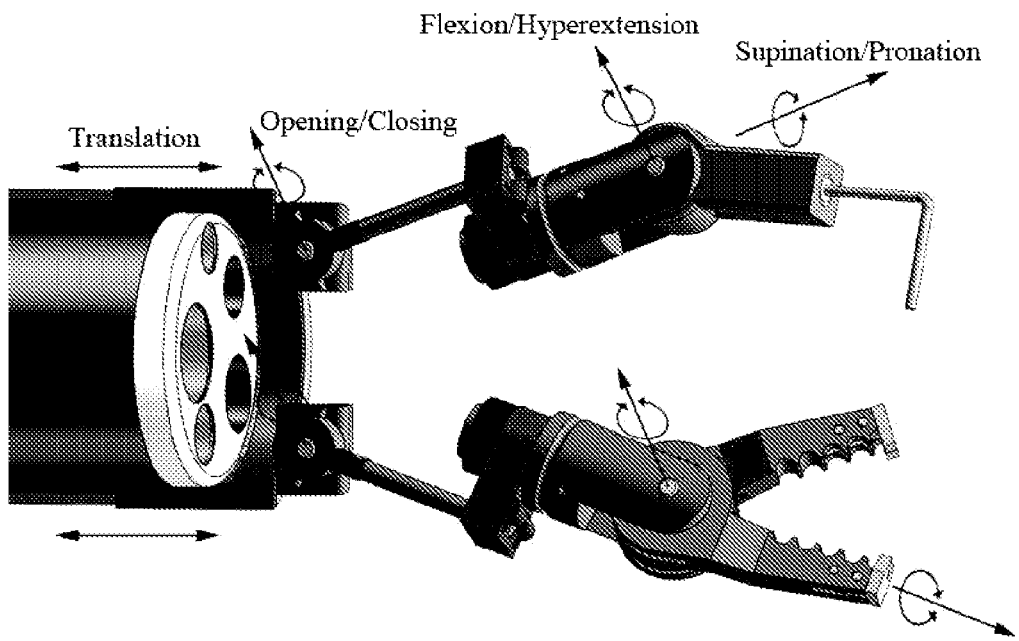
FIG. 6 is a perspective view showing the degrees of freedom of the exemplary embodiment robotic manipulator.
Figure 8:
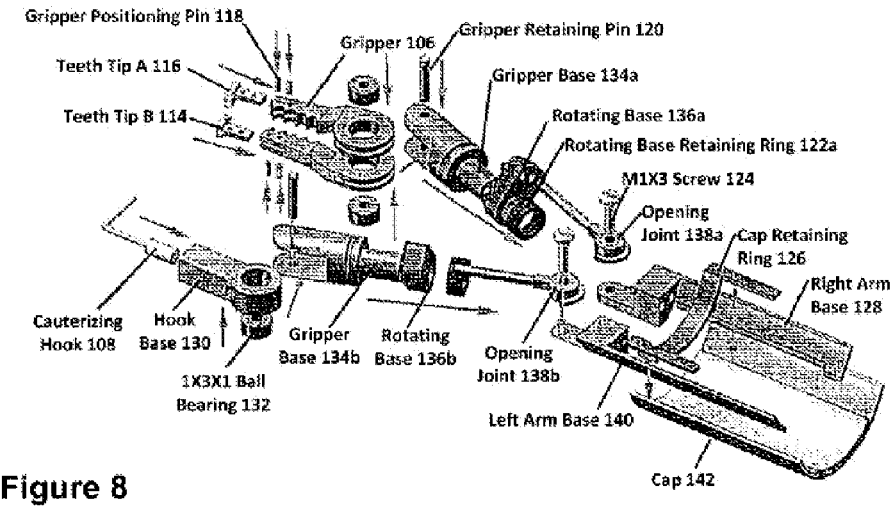
FIG. 8 is an exploded view of the exemplary embodiment robotic manipulator.

FIG. 8 shows the parts that make up the robotic manipulator 100 when the end effectors are a hook 108 and a gripper 106 and FIG. 7 shows the degrees of freedom that correspond to the exemplary robotic manipulator 100 of FIGS. 5 and 6.

Each robotic manipulator 100 has a right and a left arm base 128, 140. The joint at the arm bases 128, 140 provides a degree of freedom for controlling the translation of the arms 104a, 104b allowing forward and backward motion of the arms 104a, 104b substantially parallel to the longitudinal axis of the endoscope. The arm bases 128, 140 of each robotic manipulator 100 are anthropomorphic to the elbow, and have two orthogonal rotational opening joints 138a, 138b. These opening joints 138a, 138b provide a degree of freedom for opening and closing of the arms 104a, 104b, the opening of the arms 104a, 104b being a movement out of alignment with the longitudinal axis of the endoscope 406 (not shown), and the closing of the arms 104a, 104b being a movement to bring the arm 104a, 104b into alignment with the longitudinal axis of the endoscope 406 (not shown). The right arm base 128 and left arm base 140 are held in place by a cap 142 which is held close by a cap retaining ring 126. The two orthogonal rotational opening joints 138a, 138b are each independently fixed to one of the arm bases 128, 140 by M1X3 screw 124. Further along the arm 104a, of the robotic manipulator 100, away from the flexible member (not shown) is the rotating base retaining ring 122a which attaches the rotating base 136a to the opening joint 138a of the arm 104a. The rotating base 136a is connected to a gripper base 134a. Both arms 104a, 104b have a similar structure up to this point where the end effector 103 at the ends of the arms 104a, 104b may vary. As shown, the end effector 103 is fixed with grippers 106 at arm 104a which are used to grab tissue. The distal tip of the other end effector 103 is fixed with a hook 108 with which monopolar, cautery and cutting can be performed.

In the exemplary robotic manipulator 100 of FIGS. 5 and 6, one arm 104a ends with a gripper 106 and the other arm 104b ends with a cauterizing hook 108. The gripper base 134a of arm 104a is coupled to the gripper 106 and held in place by a gripper retaining pin 120. The gripper positioning pins 118 hold teeth tip A 116 and teeth tip B 114 at the end of the gripper 106 furthest away from the flexible member 102 in place. The joints between the teeth 114, 116 and the gripper 106, and between the gripper 106 and the gripper base 134a provide two degrees of freedom for flexion and hyperextension of the teeth 114, 116 and gripper 106 respectively. The joints in the preferred form comprise a 1×3×1 ball bearing 132. The rotating base 136a provides for a degree of freedom for supination/pronation of the gripper 106.

The other arm 104b of the exemplary robotic manipulator 100 has a gripper base 134b of arm 104b coupled to the cauterizing hook 108 by a hook base 130 and a 1×3×1 ball bearing 132b. The ball bearing 132 provides a joint at the gripper base 134b that provides for a degree of freedom for flexion and hyperextension of the cauterizing hook 108. The rotating base 136b provides for a degree of freedom for supination/pronation of the cauterizing hook 108.

Figure 9:
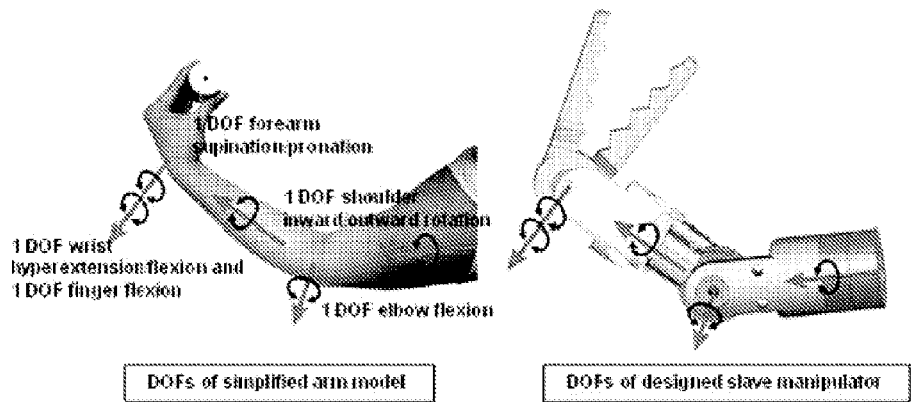
FIG. 9 is a diagram showing the similarity in design of the exemplary embodiment robotic manipulator with the human arm from the wrist to the elbow.

The nine degrees of freedom for the preferred form two arms are therefore as follows:
  i. translation forward and backward of the first arm
  ii. translation forward and backward of the second arm
  iii. opening and closing of the first arm
  iv. opening and closing of the second arm
  v. supination and pronation of the first arm vi. supination and pronation of the second arm
vii. flexion and hyperextension of the first arm
viii. flexion and hyperextension of the second arm
ix. flexion and hyperextension of the jaws of the first arm FIG. 9 shows the similarity in design of the robotic manipulator 100 with the human arm from the wrist to elbow. This similarity was intentionally provided to simplify the robotic manipulator as well as making it more nimble to perform treatment on the patient. This also makes it less tiring for the surgeon to perform the procedure since he can rest his shoulders on the flat surface.

The workspace of the robotic manipulator 100 can be seen in FIG. 10. The workspace is formed using the range of movement of the joint as simplified from −90° to 90° although the robotic manipulator 100 can move beyond this range.

Figure 11:
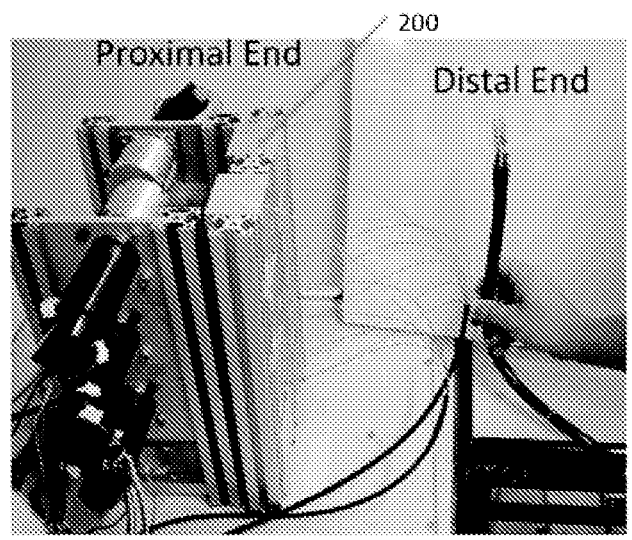
FIG. 11 is a view of an exemplary embodiment actuator for use with the system of FIG. 1.

The exemplary embodiment of an actuator 200 is shown in FIG. 11 and houses the motors, sensors and other mechatronic devices (not shown) required to actuate the robotic manipulator 100. The robotic manipulator's 100 one end is affixed to actuator 100 by way of the flexible member 102. The actuator 200 acts upon the flexible member 102 based on signals received from the controller 300.

The actuator 200 comprises a housing enclosing an electronic housing and a motor housing (not shown). The former houses the power supply, actuator amplifier, and motion controller interconnector. The latter is used to house DC motors and sheath stoppers 113, which are used to secure the sheath and tendon. The actuator housing comprises seven motors for seven motorized degrees of freedom and comprises three components: the front plates to secure sheaths, the side plates to secure the actuators and the rotating drums to secure and control the tendons. The drums are attached to the motor shaft. All the plates are restrained firmly within a structure of aluminium profiles which allows for easy disassembly if there is a need for repair and troubleshooting. The actuators are packed together in a tight configuration to save space in the operating theatre.

Figure 12:
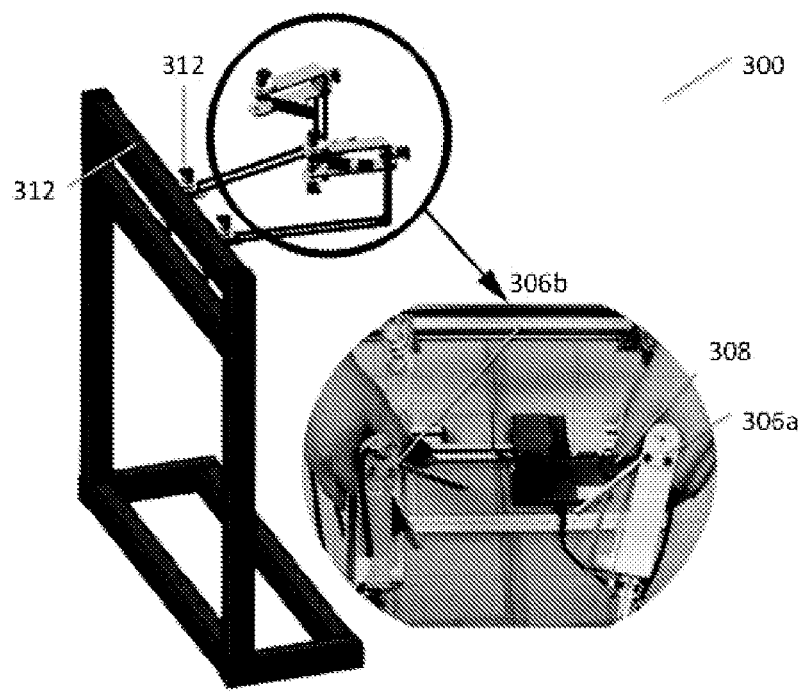
FIG. 12 is a view of an exemplary embodiment controller for use with the system of FIG. 1.
Figure 13:
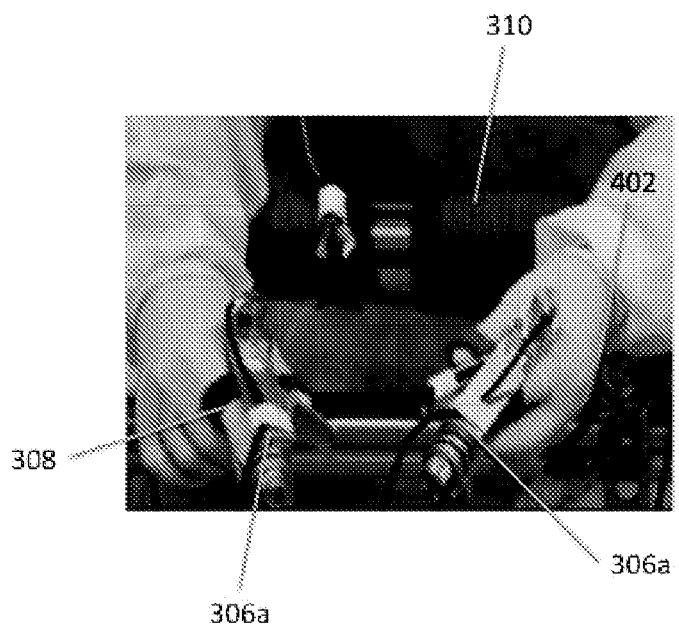
FIG. 13 is a plan view of the exemplary embodiment of a controller when in use.
Figure 14:
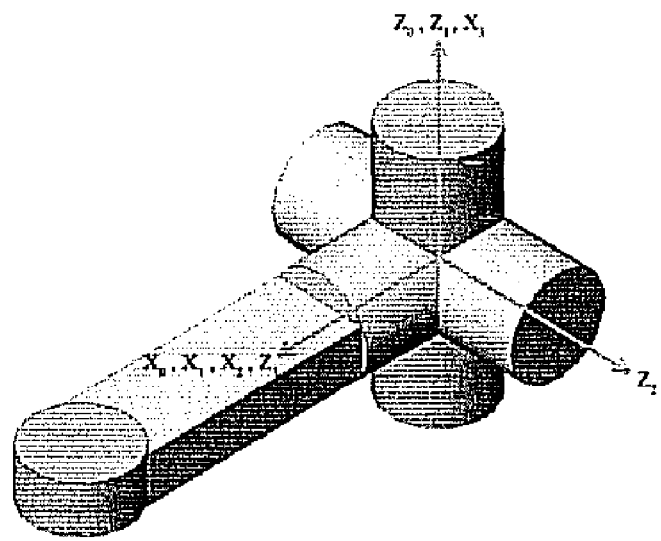
FIG. 14 is a diagram of the ball and socket joint of the exemplary embodiment controller.

The exemplary embodiment of the controller 300 is shown in FIGS. 12 and 13. The controller 300 comprises two hand-held members 306a, 306b. Each member 306 is configured for use by a user to effect movements of the robotic manipulator 100. The hand-held member 306 comprises joints providing degrees of freedom corresponding to the degrees of freedom of the robotic manipulator 100. The controller includes a microprocessor 500 configured to detect the motions of the hand-held member 306, scale the motion detected to suit the robotic manipulator 100 and transmit signals to the actuator 200 for controlling flexible members 102 connected to the robotic manipulator 100 (not shown). The hand-held members 306 include a prime mover (not shown) to receive signals from the robotic manipulator 100 and to provide feedback to a user 402 using the hand-held member 306. The hand-held members 306 comprise grippers 308 attachable to fingers of the user 402. The controller 300 further comprises an armrest 310 configured to receive a user's arm. The hand-held members 306 comprise a plurality of linkages 312 that is adjustable to suit different users. The controller 300 is kept within a housing 302. As can be seen in FIG. 14, from the design of the controller 300, the three revolute joints intercept at one point, creating a ball-and-socket joint. The position and orientation of the grippers 308 are determined by these three joints. Thus, the kinematic analysis of the controller 300 is performed on just one ball-and-socket joint.

The clinician 402 places his fingers within the finger linkages 308 of the hand-held members 306 and can freely move his wrists and fingers. With the vision system, the clinician 402 would be able to see the robotic manipulator protruding from the endoscope's distal tip. The movements of the robotic manipulator would be in strict accordance to how the clinician 402 manipulates the hand-held members 306. The hand-held members 306 are embedded with an array of linear and rotary encoders which sense the orientation of the clinician's wrists and fingers (fingers being taken to include the thumbs). This information is fed into the microprocessor 500 for further processing. The microprocessor 500 processes the received data that follow by sending commands to the actuator housing 200 to control the tendon-sheath actuation 102. Based on the force prediction modeling, the controller has also been implemented with actuators, which are able to provide force feedback to the surgeon onto two selected degrees of freedom, namely the opening and closing joints. Some or all of the joints of the devices 306 may be connected to motors which would exert resisting forces on the clinician's hand movements. This mechanical feature enables the clinician to have a force feedback during the operation. As such, the wall of the GI tract can be 'felt' by the clinician when the end effector 103 comes in contact with it. The hand-held members 306 have the nine rotational degrees of freedom, and all of the angular displacements may be sensed by rotary encoders.

Figure 15:
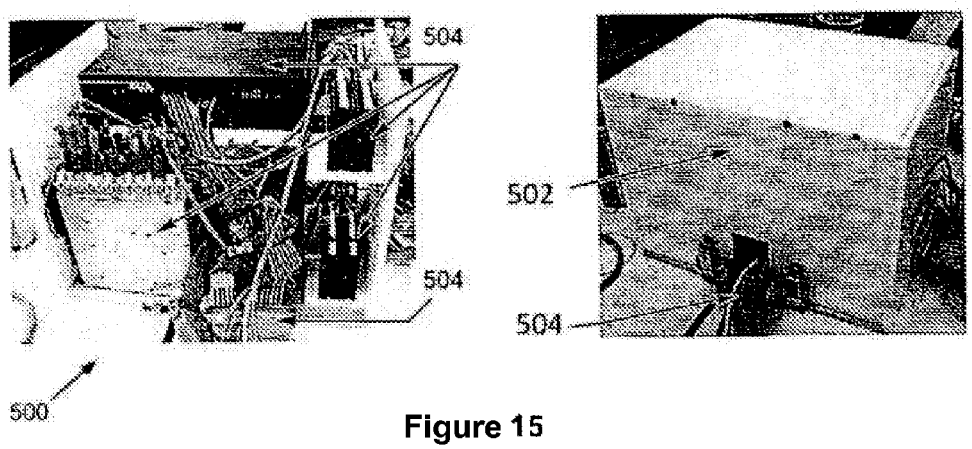
FIG. 15 is a view of an exemplary embodiment of an electronics housing of the controller.

The system according to this invention include the microprocessor 500 as shown in FIG. 15, which comprises a computer (not shown) that does the mapping between the readings of the controller 300 as well as an electronic housing 502 that comprises all the relevant wirings 504 for the system to work such as amplifiers and power supplies and protect them from the outside elements.

The systems, devices and methods of the various exemplary embodiments of applicant's robotic system in tandem with current flexible endoscopes. Because the surgical procedures would be performed through natural orifices, the systems, devices, and methods of applicants robotic system can perform what may be characterized as "no-hole surgery", which is less invasive than key-hole surgeries.

The robotic system may be used for procedures other than those of the GI tract. It may be used for any surgical procedure able to be performed with flexible scopes. These include appendectomy (removal of appendix), removal of gall bladder, tying of fallopian tubes, and so forth. The robotic system may give the surgeon more dexterity and manoeuvrability.

EXAMPLES

Example 1

Each ESD in live animal was repeated using the conventional endoscope. The main outcome measures were: (i) time required to complete the submucosal dissection of the entire lesion, (ii) dissection efficacy, (iii) completeness of the excision of the lesion, and (iv) presence or absence of perforation of the wall of the stomach.

Submucosal dissection time was defined as the time from activation of the endoscopic dissecting instrument to completion of excision of the entire lesion. Assessment of dissection efficacy was based on scoring of efficiency of two related task components—grasping and cutting of tissue—on a graded structured scale from 0 to 2, where the lowest grade, "0" means failure to grasp/cut and the highest grade "2" means a most efficient grasp/cut. Similarly, the completeness of the lesion excision is rated on a scale of 0 to 3, where "0" means failure to excise and "3" means a complete excision of the targeted lesion in one single piece. The details of the structured grading system are shown in Table 4. Grading was done by the operator and recorded on the spot. Presence of any inadvertent perforation of the stomach wall was checked by the air leak test in the Erlangan models and endoscopic visual inspection in the live animals.

TABLE 4

Structured grading system for assessing dissection efficacy and completeness of excision

| Dissection Efficacy | Score |
|---|---|
| Grasping of tissue | |
| Failure to grasp tissue | 0 |
| Able to grasp but unable to apply tissue traction | 1 |
| Able to grasp and retract tissue with some degree of tension | 2 |
| Cutting of tissue | |
| Tissue is not cut at all at standard power setting (80 W) | 0 |
| More than 3 attempts to cut tissue at standard power setting (80 W) | 1 |
| Less than 3 attempts to cut tissue at standard power setting (80 W) | 2 |
| Completeness of excision | |
| Failed excision | 0 |
| Excision of lesion in more than 3 pieces | 1 |
| Excision of lesion in less than 3 pieces | 2 |
| Excision of lesion in 1 single piece | 3 |

For operation, the robotic system (Master And Slave Transluminal Endoscopic Robot; MASTER) comprised the dual-channel therapeutic endoscope (GIF-2T160, Olympus Medical Systems Corporation, Japan) connected to a standard endoscopy platform (EVIS EXERA II Universal Platform, Olympus Medical Systems Corporation, Japan) with high-definition visual display and real-time video recording functions. An attached electrical surgical generator regulated and monitored the power output used for the monopolar resection (cutting and coagulation). Operation was conducted through the ergonomically designed steerable motion sensing controller with two articulating arms (FIG. 5). The controller was embedded with an array of linear and rotary encoders. To operate, the operator simply fits his/her wrists and fingers into the two articulating arms and moves them in the same way he/she would to manipulate the end-effectors directly. Motions are detected by the array of sensors and actuated into force signals to drive the manipulator and end-effectors via a tendon-sheath mechanism. This allows the operator to intuitively control the operation remotely. The controller and the robotic manipulator are both equipped with nine rotational degrees of freedom.

The reference system used was a standard conventional therapeutic endoscope (GIF-2T160, Olympus Medical Systems Corporation, Japan) with the usual accessories such as the insulation-tipped (IT) diathermic knife (Olympus Medical Systems Corporation, Japan) and injection needles.

Five Erlangen porcine stomachs and five pigs aged between 5 to 7 months old, and each weighing about 35 kg were used and ESD was first performed on the Erlangan models, and then on each of the live pigs, consecutively using the robotic system of the present invention (MASTER). For comparison purpose, the ESD procedures in the same 5 live pigs were repeated using the conventional endoscope.

Fresh porcine stomach was mounted on a specially designed dissection platform to simulate its normal orientation in the body. A standard dual-channel therapeutic endoscope was then passed into the stomach through an overtube and the stomach was flushed with normal saline. Using the IT diathermic knife, artificial gastric lesions approximately 20 mm in diameter were marked by means of spotty cautery on the mucosa of the cardia, antrum and body of the stomach. Before the ESD, each of these lesions was elevated by submucosal injection of a cocktail of 40 ml normal saline and 2 ml of 0.04% indigo carmine. The conventional endoscope was then removed and a dual-channel therapeutic endoscope with the robotic system of the present invention mounted was introduced into the stomach. Using the robotic grasper to hold the elevated lesion, a peripheral mucosal incision was made using the monopolar electrocautery hook (Power setting, 80 W) at a circumferential margin of 1 cm from the demarcated area. Once completed, the mucosal flap was lifted using the grasper. Cutting line visualization was maintained as the monopolar electrocautery hook was applied underneath the flap in a direction parallel to the muscle layer to cut the lesion through the submucosal plane. Dissection was executed in a single lateral direction until completion and the entire lesion was excised enbloc. On completion of the experiment, the stomach was insufflated with air to detect for leak due to any inadvertent perforation caused during ESD. The stomach was then cut and opened for inspection of completeness of lesion resection.

For study in live animals, the pig was food deprived for 18 hrs just before the procedure. The animal was sedated for pre-surgical preparation. A preanesthetic cocktail of ketamine 20 mg/kg and atropine 0.05 mg/kg intramuscularly was adminstered, following which anesthesia was induced with 5% intravenous isoflurane. The animal was then intubated with an endotrachael tube. General anesthesia with 1-2% isoflurane followed. Throughout the operation, oxygen was administrated to the animal at a flow rate of 2.0 liter/minute, while heart rate and SpO2 were monitored every 20 minutes.

As with the Erlangan models, gastric lesions were marked using the IT knife and lesions were elevated by a submucosal injection of a cocktail of 40 ml normal saline and 1 ml indigo carmine (40 mg/5 mL). ESD was performed in a similar manner as described under the method for Erlangan models and the entire lesion was excised enbloc and retrieved through the mouth. Hemostasis, where necessary, was achieved with the electrocautery hook (Power setting, 60 W). In each animal, the experiment was repeated on one other lesion using the conventional endoscope, in which case, an IT knife was deployed through the accessory channel of the endoscope to do the dissection. After the operation, the stomach was visually inspected for signs of perforation. Once done, the animal was euthanized according to IACUC approved protocol.

Data Capture and Analysis

During the experiment, an independent assessor recorded the sequence and timing of all pertinent tasks. The collected data was entered into an Excel spreadsheet and data was analyzed using simple descriptive statistics. The average time taken to dissect the entire lesion in Erlangan models and live animals were separately computed. The mean dissection time taken by the MASTER was compared to that taken by conventional endoscopy method using simple student's t-test.

Results

In the study on Erlangen porcine stomach models, a total of 15 gastric lesions located at the cardia, antrum, or body of the stomach were successfully excised in single piece following submucosal dissection using the MASTER, with no incidence of gastric wall perforation. The mean dimension of the excised specimens was 37.4×26.5 mm. Mean submucosal dissection time was 23.9 min (range, 7-48 min). There was no significant difference between the dissection times of lesions at the different locations in the stomach (P=0.449).

Figure 16:
FIG. 16 is an image showing the vision from an endoscope during endoscopic submucosal dissection (ESD)
Figure 17:
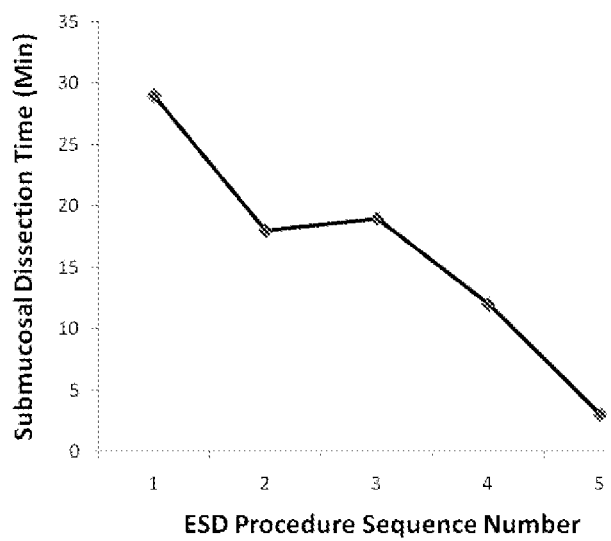
FIG. 17 is a graphical representation of submucosal dissection times for a consecutive series of five trial ESD procedures in pigs.
Figure 18:
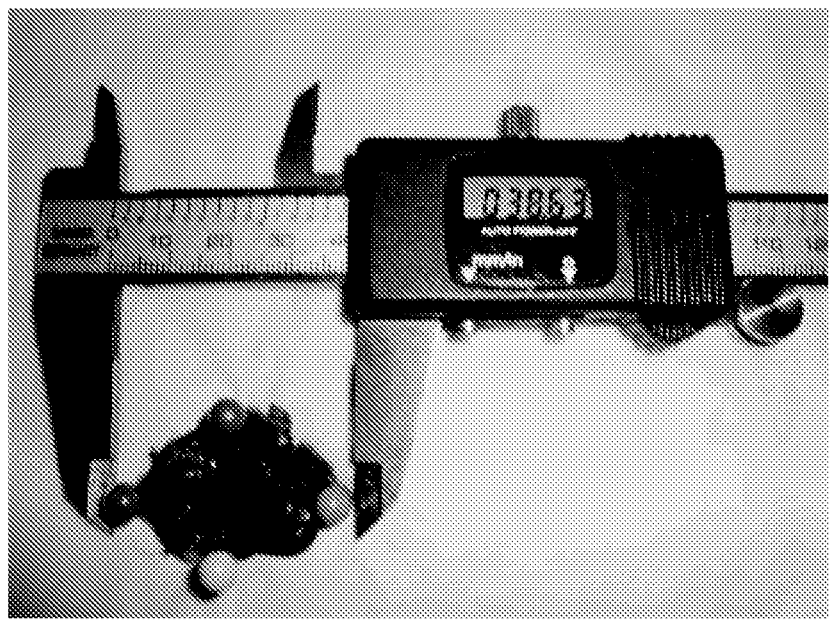
FIG. 18 is an image of an excised gastric lesion.
Figure 19:
FIG. 19 is a picture of the ex vivo test during grasping and cutting process.

In the experiment on five live pigs, the MASTER took a mean of 16.2 min (range, 3-29 min) to complete the submucosal dissection (FIG. 16). The dissection time was 29, 18, 19, 12, 3 min for the consecutive series of five animals, respectively, in the order they were performed (FIG. 17). This compares with a similar mean dissection time of 18.6 min (range, 9-34 min) taken by the conventional endoscopic system with an IT knife deployed through its accessory channel (P=0.708). The dissection time for ESD performed using the conventional method in five consecutive animals was 9, 23, 34, 15, 12 min, respectively. In both series of ESDs performed, all lesions were efficiently excised enbloc. The mean dimension of the specimens resected by the MASTER was 37.2×30.1 mm; those resected by conventional endoscopy with IT knife averaged 32.78×25.6 mm. A sample specimen is shown in FIG. 18. There was no incidence of excessive bleeding or gastric wall perforation in either group of animals.

In all the experiments conducted using the MASTER, control of the robotic manipulator was easily achieved by the operator steering the ergonomically designed motion sensing controller. Triangulation of the two arms was achieved with ease and robotic coordination of the two end-effectors was precise. Enbloc resection of all lesions was easily performed by the robotic monopolar electrocautery hook cutting set at a power of 80 W, attaining good cutting efficiency (Grade 2) throughout. In all cases, it took the operator less than three attempts to cut through the gastric submucosa. Grasping and retraction tension of the robotic grasper performed just as well (Grade 2); the operator could grasp and retract tissue with some degree of tension throughout the procedure. All surgical maneuvers were accurate; end-effectors' aims were on target all the time and no untoward incident such as injury to surrounding tissue and vasculature occurred.

It is demonstrated for the first time in live animals how MASTER can mitigate some of the fundamental technical constraints in endoscopic surgery to facilitate performance of ESD, a technically challenging endoluminal procedure. MASTER represents a breakthrough deconstruction of the endoscopy platform, by introducing robotic control of surgical tools and tasks through an ergonomic human-machine interface built around the original endoscopic paradigm. It separates control of instrumental motion from that of endoscopic movement such that surgical tasks may be independently executed by a second operator via a human-machine interface. With it, endoscopically deployed instruments can be independently controlled, allowing thus bimanual coordination of effector instruments to facilitate actions such as retraction/exposure, traction/countertraction, approximation and dissection of tissue. Robotic technology increases the degrees of freedom for mobility of endoscopic instruments deployed at the distal end of the endoscope. With nine degrees of freedom at the manipulating end of the robotic manipulator, MASTER allows the operator to position and orient the attached effector instrument at any point in space. This enables triangulation of surgical end-effectors otherwise not possible with standard endoscopy platforms. Through the master-slave system, significant force could be exerted to the point of action, allowing the end-effectors to effectively manipulate and dissect the tissue, as in the submucosal dissection in the present performance of ESD.

MASTER has clear advantages over standalone surgical robots as it is not as bulky and is designed to be adaptable to any standard dual channel endoscope. It requires a minimum of just two operators to perform an endoscopic surgery, just as in the performance of the ESD we just described. With the precision and efficiency of the MASTER, the entire ESD operation could potentially be completed in a very short time. Although in this pilot trial, no significant difference was seen in the mean submucosal dissection times taken by MASTER and the conventional endoscope with IT knife, it is believed the system could perform better and faster once operators become more accustomed to its use. This preliminary evaluation of MASTER for endoscopic surgery is limited in the sense that operators have yet to fully master the operation of the new equipment. The present performance results reflect just the early part of a learning curve. In the present series of live animal studies, the first dissection took 29 minutes, but the dissection time subsequently dropped to 3 min at the final or $5^{th}$ procedure. As operation of the MASTER is intuitive, it is not difficult for a novice to master the skills. Implementation of its use in endoscopic surgery will therefore not require as long a learning curve as with conventional endoscopy systems. Despite this being the initial trial application of the MASTER, no untoward injury to surrounding organs, tissue or vasculature occurred.

MASTER is a promising platform for efficient and safe performance of complex endoluminal surgery such as ESD. It is expected that with further developments such as refinement of the system, incorporation of haptic technology for tactile and force feedback, and addition of adaptable auxiliary devices, as well as a complete armamentarium of useful swappable end-effectors, the functionality of the endosurgical system would be greatly improved and expanded to adequately support both endoluminal and transluminal surgery.

Example 2

Before the experiment was performed on living animals, MASTER was first tested on explanted porcine's stomach. The main objective of the ex vivo experiment was to test the capability of the system in grasping and cutting performance. The grippers must provide enough force for grasping along with manipulating the tissue while the hook must be able to perform the cut at the desired site of the tissue. The test also establishes the teamwork and the cooperation between the endoscopist who has more than 20 years of clinical experience and the surgeon who controls the controller with less than 5 years of experience. With 15 times of training with explanted tissues, the result showed the feasibility of the system before being conducted in real animal.

The liver wedge resection procedure was chosen to test the feasibility of the system to perform NOTES. The in vivo test was performed at the Advance Surgical Training Center, National University Hospital in Singapore with the help of experienced endoscopists and surgeons. Using the controller and robotic manipulator manipulator was successfully used to perform two in vivo liver wedge resections on animals through NOTES procedure. To perform the liver wedge resections, the manipulator firstly performed gastrotomy, in which an incision is made from within the stomach to access the peritoneal cavity of a live pig. Once the robot is inside the peritoneal cavity, the endoscopist would control the endoscope to reach the liver side to perform the liver wedge resection. The grippers of the manipulator then held onto the edge of the liver while the electrocautery hook proceeded to cut out a piece of the liver. During this procedure, the grippers had to grasp the edge of the liver firmly to provide tension for the cauterizing cut to be effective.

The liver resection process took approximately 9 minutes for each of the two in vivo animal trials. After the liver wedge resection was perform, with the grasper still holding onto the resected tissue, the hook was still free to perform haemostasis at the freshly cut portions of the liver to arrest bleeding. The surgeon then removed the robot from the porcine and retrieved the liver wedge for analysis. The dimensions of the liver pieces taken out are shown in Table 5. Two trials were merely performed due to stringent regulation, however to further justify the performances of the system; more animal trials would be conducted in the future.

TABLE 5

The time required and the size of the liver wedge resection

|  | Time (mins) | Length (mm) | Width (mm) |
|---|---|---|---|
| Pig 1 | 8.5 | 21 | 10 |
| Pig 2 | 8.2 | 14 | 8 |

Ex vivo and in vivo experiments were conducted. Two liver wedge resections were performed successfully with the MASTER system. The results showed the potential of the system to be implemented in other applications of NOTES such as removal of the appendix and gall bladder.

In the near future, the size of the robotic manipulator would be further reduced to enable the change of the end effectors intraoperatively The force feedback will be evaluated and applied to the rest of the degrees of fredom. The next challenge would be to perform suturing with two pairs of graspers manipulator and to perform more complicated NOTES procedures like cholycystectomy and splencetomy with the MASTER system.

Example 3

In order to have a successful application of MASTER in NOTES, ESD was done. With the robotic manipulator, intensive experiments were conducted to verify the feasibility of the robotic system. Together with the help of experienced endoscopists, 15 ex vivo ESDs, 5 in vivo ESDs and 2 in vivo NOTES had been performed successfully on pigs. Before the trials, practice sessions with ex vivo pigs' stomachs were conducted with the surgeon to establish the necessary steps for the ESD and NOTES. It also enabled the endoscopists to understand the capability and limitation from the endoscope and the robot.

Since the prototype is used only on animals, the robots are tentatively just cleaned thoroughly with soap, water and brush and subsequently reused for further trials. In future the robotic manipulator could be designed to be disposable after a single use to ensure it is sterilized effective for human patients.

ESD with MASTER

The finalized steps for robotic ESD are given as follows. FIG. 16 provided is the actual view recorded from the endoscope during one of the ESD.

Firstly, the endoscopist has to spot the lesions where the ESD should take place with a conventional endoscope. When the surgeon has located the lesion, he proceeds with marking of the surroundings of the flesh with a conventional needle knife set at coagulating mode. This is to ensure both the endoscopist and surgeon are clear about where the procedure is worked on and do not cut too excessively or too little.

Next the endoscopist uses an injector to inject saline at the lesion to separate the muscle and mucosal layer. This procedure is to ensure the tool does not overcut into the muscle layer and cause excessive damage and bleeding to the patient. The saline is also colored with Methylene Blue for better vision clarity during the subsequent procedures.

After the injection, the conventional endoscope is taken out and replaced with the robotic manipulator. Both the endoscopist and surgeon then try to perform the peripheral cut on the lesion. This cut is performed using the robotic system to cut a complete circumference around the lesion. This makes the lesion region loose from the surrounding and therefore easier to be manipulated by the robot. The peripheral cut also ensures the cut is localized within the region and not cut excessively into the other healthy site.

For this procedure, the endoscopist and surgeon try to position the hook slightly above the lesion before the hook pokes into the lesion using electro-cautery. Once the hook is through, the endoscopist then moves the endoscope and the hook to cauterize along the surrounding of the lesion. During this time, the surgeon has to change the orientation of the hook if necessary to facilitate the peripheral cut.

After the peripheral cut, the endoscopist and surgeon has to go around the lesion to ensure that the peripheral cut for the whole circumference is complete. If there is a site which is still attached to the lesion, the surgeon then try to finish the cut with the hook. This step is important since any remaining ridges on the lesion can cause the subsequent steps to be more difficult.

After the peripheral cut is complete, the endoscopist proceeds with the actual removal of the lesion. The robotic manipulator then goes to the top left hand corner of the lesion and the gripper grasps onto the former. This exposes the flesh below the mucosal layer and the hook can proceed with cauterizing the lesion off. If there is a need, the endoscopist can relocate to another location for the robotic manipulator to work on. The surgeon continues cauterizing until the whole lesion is cut loose from the stomach. If there is bleeding, the hook can acts as a coagulator to seal the blood vessels.

The view of the site after the procedure can be seen in the above figure. No perforation of the stomach is observed and the marked lesion is cleanly removed. ESD procedure had been successfully performed with the robotic system.

Tables 6 and 7 below show the summary of the results for the fifteen ex vivo animal trials and five in vivo animal trials performed by the system.

TABLE 6

Results for 15 ex vivo ESD animal trials

| Experiment Number | Dissection Time (min) | Tissue Size (mm) | |
|---|---|---|---|
| | | Length | Width |
| Lesion 1A | 10 | 50 | 40 |
| Lesion 1B | 41 | 40 | 30 |
| Lesion 1C | 48 | 32 | 28 |
| Lesion 2A | 48 | 27 | 20 |
| Lesion 2B | 22 | 23 | 18 |
| Lesion 2C | 15 | 46 | 25 |
| Lesion 3A | 8 | 25 | 21 |
| Lesion 3B | 26 | 40 | 27 |
| Lesion 3C | 41 | 45 | 28 |
| Lesion 4A | 7 | 50 | 26 |
| Lesion 4B | 24 | 37 | 33 |
| Lesion 4C | 9 | 30 | 26 |
| Lesion 5A | 22 | 48 | 26 |
| Lesion 5B | 25 | 39 | 26 |
| Lesion 5C | 12 | 29 | 24 |

TABLE 7

Results for 5 in vivo ESD animal trials

|  | Dissection Time (min) | Length (mm) | Width |
|---|---|---|---|
| Pig 1 (Conventional) | 14 | 29.1 | 22.2 |
| Pig 1 (Robotic) | 40 | 38.6 | 25.2 |
| Pig 2 (Conventional) | 26 | 50.2 | 33.0 |
| Pig 2 (Robotic) | 29 | 33 | 30 |
| Pig 3 (Conventional) | 34 | 34.7 | 32.9 |
| Pig 3 (Robotic) | 19 | 42.8 | 25.7 |
| Pig 4 (Conventional) | 15 | 21.8 | 17.2 |
| Pig 4 (Robotic) | 12 | 33.0 | 29.8 |
| Pig 5 (Conventional) | 12 | 28.4 | 22.9 |
| Pig 5 (Robotic) | 3 | 28.8 | 22.9 |

From the results shown, it was observed that initially the manipulator took much more time in performing ESD as compared with conventional methods. However, after more practices, refinement of the procedure and improved communication between the endoscopist and surgeon, the time taken for the procedure reduced to 3 minutes compared with 12 minutes from the conventional ESD. The average size for the lesion is about 35.24 mm by 26.72 mm. The procedure also shows no complication, perforation and the sample lesion taken out is in one piece. This study was performed on live pigs and the results show the method is feasible and could be an improvement in performing ESD.

NOTES with MASTER

The robotic system was used to perform liver wedge resection on the live pigs. After the system gains access into the live pig's stomach, the endoscopist tries to establish the position and orientation of the stomach before using the robot to perform gastrotomy. Gastrotomy requires the robot to cut a hole through the stomach wall to access the peritoneal cavity of the pig.

Once the system is inside the peritoneal cavity, the manipulator faces the liver and proceeds with the liver wedge resection. The endoscopist determines the site where the cut should take place. The cauterizing should begin close to the edge of the liver instead of the edge to ensure there is a tension at the top end of the cut tissue. During this procedure the gripper has to grasp the edge of the liver to provide tension for the cauterizing cut to be effective. The surgeon and endoscopist then try to cauterize the liver till only the top and bottom edges are left.

After they ensure the cut in the middle is complete, the two edges are then cut. The surgeon can choose to cut the top edge or bottom edge to complete the liver resection. In the first trial, the endoscopist and surgeon chose to remove the top edge first before cutting through the bottom edge.

With the gripper still holding the cut liver wedge, the hook then proceeds with the coagulation of the liver surface to stop the bleeding. The surgeon then removes the robot from the pig and retrieves the liver wedge for analysis. The perforated cut on the stomach wall can then be mended using conventional methods such as haemoclips etc.

Table 8 shows the results for the two trials for NOTES. The time taken to cut through the stomach, cut off the liver wedge and coagulating took approximately 8-9 minutes.

TABLE 8

Results on time taken for liver wedge resection and size

|  | Time (mins) | Length (mm) | Width (mm) |
|---|---|---|---|
| Pig 4 (Robotic) | 8.5 | 21 | 10 |
| Pig 5 (Robotic) | 8.2 | 14 | 8 |

Example 4

Tension Study of Tendon and Sheath

The motion of the slave manipulator is completely controlled by the surgeon and therefore there is no autonomy for the motion of the slave manipulator. Hence is it imperative for the surgeon to obtain the correct and necessary information to make the best decision in carrying out the task. Due to the limited depth perception from the 2D image, the surgeon cannot tell if the slave manipulator is pushing at the wrong place excessively.

To compensate for the loss of depth perception, it is envisaged that force feedback could be used to rely useful information about the procedure back to the surgeon. However, due to size constraints, it is impractical to attach even miniaturized and sophisticated sensors at the end effectors for the slave manipulators. Furthermore, the sensors would have to be sterilized prior the surgical intervention. Therefore, a method of force prediction of the tendon sheath mechanism, which does not require installing any sensor at the slave manipulator, is proposed. The method utilizes the theoretical modelling of the characteristic of the tendon sheath actuation to predict the distal force and elongation during the various phases of the actuation. The force prediction method requires a set of external sensors located at the actuator housing. The output reading of the sensor could be used to predict the force experienced by the end effectors. The result of the force prediction is used as the input for the actuator at the master console in order to provide the force sensation to the surgeon. Therefore by using this force prediction method, the surgeon is able feel the force that the slave manipulators are exerting on the surroundings. This ensures the surgeon does not cause unnecessary trauma to the patient body and also ensures that the robotic system does not break down due to excessive tension on the tendon. With this force feedback system in place, it is expected that the surgeon could perform a NOTES procedure in a faster, safer and more consistent manner.

Figure 20:
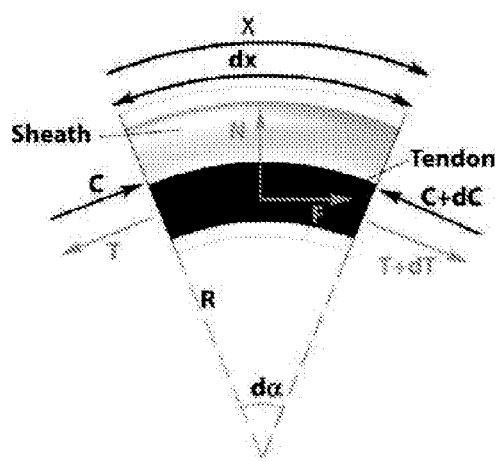
FIG. 20 is a model of a small section dx of a tendon and sheath.

In the following description, the sheath is assumed to be bent with a constant radius of curvature as seen in FIG. 20. In our model $\mu$ is the friction coefficient between the sheath and the tendon, N is the normal force the sheath is exerting on the tendon in this unit length, T is the tension of the tendon, C is the compression force experienced by the sheath, $T_{in}$ is the tension at one end of the sheath, R is the bending radius of the tendon, x is the longitudinal coordinate from the housing end of the sheath to the present location, F is the friction between the tendon and the sheath in this unit length. To simplify our model, $\mu$ can be assumed as the dynamic friction when the tendon is moving within the sheaths and it is a constant.

Using the force balance equations on the tendon for a small section dx, corresponding to the angle d$\alpha$, we have $$Td\alpha = -N, \; d\alpha = dx/R, \; F = \mu N \text{ and } dT = F$$

thus obtaining $$\frac{dT}{dx} = \frac{\mu}{R}T \qquad (1)$$

$$T(x) = T_{in}e^{-\frac{\mu}{R}x}$$

Next, the force balance equation is applied on the sheath. Forces N and F for the tendon are equal and opposite to the forces N and F of the sheath since they are reacting against each other. Since the tendon thickness is close to the inner diameter of the sheath and the segment of tendon sheath is significantly small, the angle of both tendon and sheath is assumed to be the same. Therefore we have $$C = -T, \; dC = -dT \qquad (2)$$

The compressive force measured at the proximal end of the sheath is the same as the tension measured from the tendon at the same end. This result is easily verified by experiments.

Figure 21:
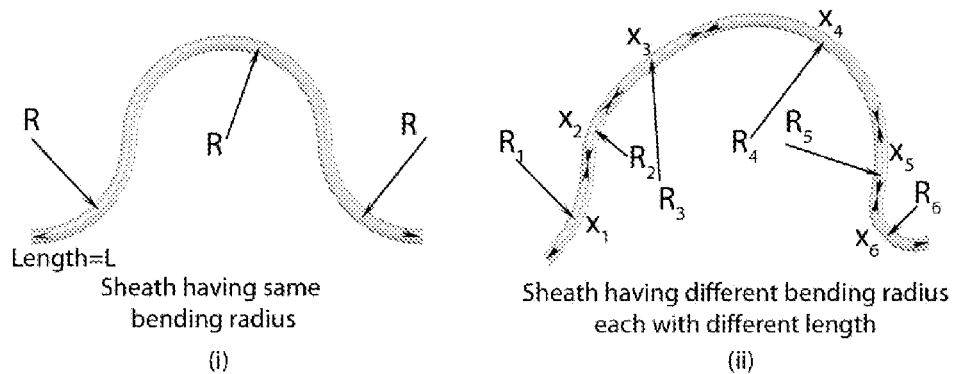
FIG. 21 is a simplified model of the sheath compared with a generic sheath.

The theory presented so far applies only to sheath and tendon with a fixed curvature throughout its length, as shown in FIG. 21. In general, the sheaths are free to move and the curvature is different throughout the whole length. This is modeled as a sheath having n sections, each having a different radius of curvature $R_1$ to $R_n$ and a displacement of $x_1$ to $x_n$ from the housing. In this case equation (1) becomes $$T(x) = T_{in}\left(e^{-\frac{\mu}{R_1}x_1 - \frac{\mu}{R_2}(x_2-x_1)\ldots\frac{\mu}{R_{n-1}}(x_{n-1}-x_{n-2})-\frac{\mu}{R_n}(x-x_{n-1})}\right) \qquad (3)$$

$$(x_{n-1} < x < x_n)$$

To predict the tension at the end of the sheath, expression (3) can be simplified as $$T_{out} = T_{in}e^{-K} \qquad (4)$$

$$\text{where } K = \mu\left(\frac{x_1}{R_1} + \frac{x_2-x_1}{R_2} + \ldots + \frac{x_n-x_{n-1}}{R_n}\right)$$

represents the effective friction between the tendon and sheath. It is important to note that, if the sheath does not change its shape, K is a constant. It is impossible to determine $x_i$ and $R_i$, but there is a way to make use of this equation as described later.

Another relevant parameter is the elongation of the tendon and sheath system under a certain force. The study is initially applied to a sheath with a fixed bending radius applying it to a generic sheath. Using e as the tendon elongation and E as the combined stiffness of the tendon and sheath, $$e(x) = \frac{T(x)}{E} \qquad (5)$$

where the tendon tension varies with x. To obtain the total elongation, equation (5) must be integrated over the length of the tendon sheath system, thus obtaining $$e_{total} = \frac{1}{E}\int_0^x T_{in}e^{-\frac{\mu}{R}x}dx \qquad (6)$$

This is actually the area under the graph of the tension distribution T divided over the constant E. The analytical solution is $$e_{total} = \frac{T_{in}R}{E\mu}\left(1 - e^{-\frac{\mu}{R}x}\right) \qquad (7)$$

Another expression is $$e_{total} = \frac{R}{E\mu}(T_{in} - T_{out}) \qquad (8)$$

$T_{out}$ is the tension experienced by the tendon at the end effector. This result is slightly different from that of the prior art for two main reasons. First, pretension is not required. Second, it does not make the assumption that the force is evenly distributed within the sheath. When the system is used, it starts with zero or low pretension. In this case, two actuators are used to control one degree of freedom instead of the traditional one actuator per degree of freedom. This also simplifies the modelling of the problem, since only one tendon undergoes a tension at any given time.

The above derivation is used when both the tendon and sheath have a constant bending radius. If the sheath is modelled as having n sections, each having a different radius of curvature $R_1$ to $R_n$ and each having a displacement of $x_1$ to $x_n$, then $$e_{o1} = \frac{R_1}{E\mu}(T_{in} - T_{o1}) \qquad (9)$$

$$e_{total} = \frac{T_{in}R}{E\mu}\left(1 - e^{-\frac{\mu}{R}x}\right)$$

$$(x = x_1)$$

Where $e_{o1}$ is the elongation at $x=x_1$ and $T_{o1}$ is the tension at $x=x_1$. Similarly $$e_{total} = \frac{T_{in}}{E\mu}\left[R_1\left(1 - e^{-\frac{\mu}{R_1}x_1}\right) + R_2 e^{-\frac{\mu}{R_1}x_1}\left(1 - e^{-\frac{\mu}{R_1}(x_2-x_1)}\right)\right] \qquad (10)$$

$$(x = x_2)$$

$$\ldots$$

$$e_{total} = \frac{T_{in}}{E\mu}\left[R_1\left(1 - e^{-\frac{\mu}{R_1}x_1}\right) + \sum_{i=2}^{n} R_i e^{-\mu\sum_{j=1}^{i}\frac{x_{j-1}-x_{j-2}}{R_{j-1}}}\left(1 - e^{-\mu\frac{x_i-x_{i-1}}{R_i}}\right)\right]$$

$$(x = x_n)$$

$$e_{total} = M_e T_{in} \qquad (11)$$

Where $$M_e = \frac{1}{E\mu}\left[R_1\left(1 - e^{-\frac{\mu}{R_1}x_1}\right) + \sum_{i=2}^{n} R_i e^{-\mu\sum_{j=1}^{i}\frac{x_{j-1}-x_{j-2}}{R_{j-1}}}\left(1 - e^{-\mu\frac{x_i-x_{i-1}}{R_i}}\right)\right]$$

where $M_e$ represents the effective elongation constant of the tendon sheath system. It is a constant if the shape of the tendon and sheath remains the same.

Figure 22:
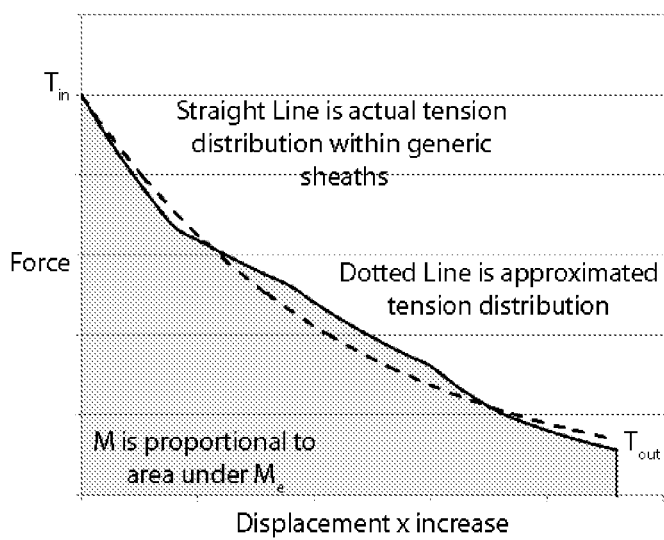
FIG. 22 is a graphical representation of $M_e$ and K.

The relationship of K and $M_e$ with $T_{in}$ is expressed in FIG. 22. The full line curve represents the actual tension distribution for a generic sheath at $T_{in}$. The dotted line represents the approximate solution coming from equation (4) as displacement x increases. The value of $M_e$ is proportional to the area under the straight line curve and it is an indication of sheath deformation. In the experimental setup section, the approach to find K and $M_e$ is discussed in detail. It should be noted that just the values for the force at the two ends are necessary for control.

By approximating the original curvature to the one characterized by K, the relationship, between $M_e$ and K can be retrieved by evaluating the area underneath $T_{in}e^{-K}$ multiplied by 1/E, $$M_e T_{in} = \frac{T_{in}L}{EK}(1 - e^{-K}) \quad (12)$$

$$e^{-K} = -\frac{M_e E}{L}K + 1 \quad (13)$$

It is seen that $M_e$ and K are dependent on each other and the value of $M_e$ is enough to approximate K and vice versa. E is the Young's modulus or stiffness of the tendon and therefore is the same regardless of the shape. There is no readily available solution for equation (13) and numerical methods, such as Newton-Raphson or the Golden Section method have to be used.

Figure 23:
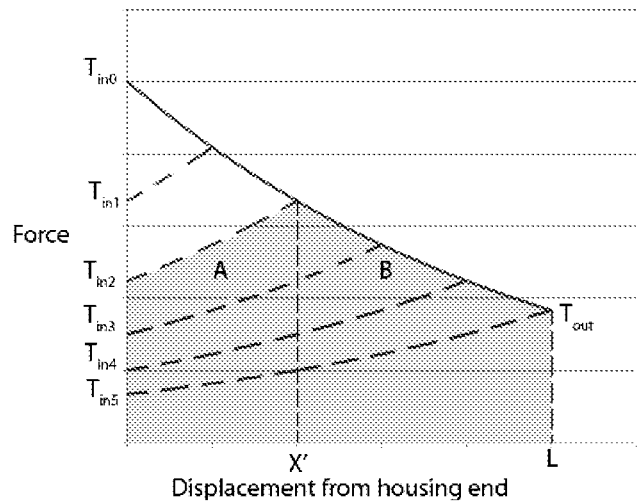
FIG. 23 is a graphical representation showing the gradually reducing $T_{in}$ and the tension distribution within the sheath.

However, this result is relevant only when the system undergoes a pulling phase. In the case the tendon is just released after being pulled, the system does not immediately go into the release phase. It undergoes a transitional phase from pulling to releasing. FIG. 23 shows the tension distribution within the sheath as the housing force is gradually reduced. The first effect of a decrease in $T_{in}$ is a reduction of the tension within the sheath, while the tension at the end effector is not affected. Let X' be the distance from the proximal end where the highest amount of tension within the sheath. As $T_{in}$ decreases, X' moves further from the proximal end and closer to the end effector. Only when X' reaches the end of the sheath, then $T_{out}$ starts to decrease. This is the so called "backlash" of the tendon sheath system.

During the transitional phase, $T_{out}$ remains constant until $T_{in}$ reduces to $T_{in5}$, as shown in FIG. 23. Therefore $$T_{out} = T_{in0}e^{-K} \quad (14)$$

where $T_{in0}$ is the highest value of the tension recorded at the housing before it starts to loosen.

Differently from tension, the elongation varies during the transitional period. The area under the tension distribution curve is proportional to the elongation of the tendon and sheath and it undergoes relevant variations. This change in the area is observed under the shaded graph of FIG. 23.

The elongation of the tendon during the transitional phase is derived in two steps. First, the displacement X' is calculated. The second step is to evaluate the elongation under the shaded areas A and B of the curve. To perform this step, we take advantage from the curvature approximated by K.

Using L as the length of the whole sheath, $$T_{in}e^{\frac{K}{L}X'} = T_{in0}e^{-\frac{K}{L}X'} \quad (15)$$

$$X' = \frac{L}{2K}\ln\frac{T_{in0}}{T_{in}} \quad (16)$$

When X'=L, $T_{in}=T_{in0}e^{-2K}$ is the force that the tension at the housing side has to release before $T_{out}$ reduces. This value can be calculated and used online in order to infer if the system is still working within the backlash region.

Now a way to calculate the elongation coming from area A of FIG. 23 is presented. Using A be the area underneath the tension distribution from x=0 to x=X', $$\text{Area } A = \int_0^{X'} e^{-\frac{K}{L}}dx \quad (17)$$

$$\text{Area } A = \frac{L}{K}(1 - e^{-\frac{K}{L}X'})$$

Similar to the derivation of equation (6), the elongation under Area A is given by the area of the curve multiplied by the highest tension in A, divided by E. In this case, the highest tension within A is $$T_{in}e^{\frac{K}{L}X'}.$$

The resulting equation becomes $$e_A \approx \frac{T_{in}Le^{\frac{K}{L}X'}}{EK}(1 - e^{-\frac{K}{L}X'}) \quad (18)$$

The elongation caused by area B is proportional to the area under the curve from x=X' to x=L.

$$\text{Area } B = \frac{L}{K}(1 - e^{-\frac{K}{L}(L-X')}) \quad (19)$$

$$e_B \approx \frac{T_{in}Le^{\frac{K}{L}X'}}{EK}\left(1 - e^{-K\left(1-\frac{X'}{L}\right)}\right)$$

The combined elongation for the two areas become $$e_{total} \approx \frac{T_{in}L}{EK}\left(2e^{\frac{K}{L}X'} - 1 - e^{\left(-K+\frac{2KX'}{L}\right)}\right) \quad (20)$$

By substituting $$X' = \frac{L}{2K}\ln\frac{T_{in0}}{T_{in}}$$

into the equation above, we obtain $$e_{total} \approx (2\sqrt{T_{in0}T_{in}} - T_{in} - T_{in0}e^{-K}) \quad (21)$$

Release Phase

If $T_{in}$ keeps decreasing after the transitional phase, the tendon sheath goes into the release phase. As $T_{in}$ decreases, $T_{out}$ starts to decrease as well. The method to derive the end effector force and the elongation is by changing the side that is "pulling" to be at the end effector instead of the housing. Therefore, $$T_{out} = T_{in}e^{K} \quad (22)$$

$$e_{out} = M_e T_{in}e^{K} \quad (23)$$

Release to Pull Phase

Similar to the transition from pulling to release, the tension at the end effector remains the same throughout the whole phase.

$$T_{out} = T_{in0} e^{-K} \quad (24)$$

Where $T_{in0}$ is the lowest point of the tension recorded at the housing before it starts to tighten. The steps to find the deformation of the tendon and sheath are the same as the transition phase from pulling to release. The final equation for the elongation is shown below.

$$e_{total} \approx \frac{L}{EK}\left(T_{in} - 2\sqrt{T_{in}T_{in0}} + T_{in0}e^{K}\right) \quad (25)$$

Figure 24:
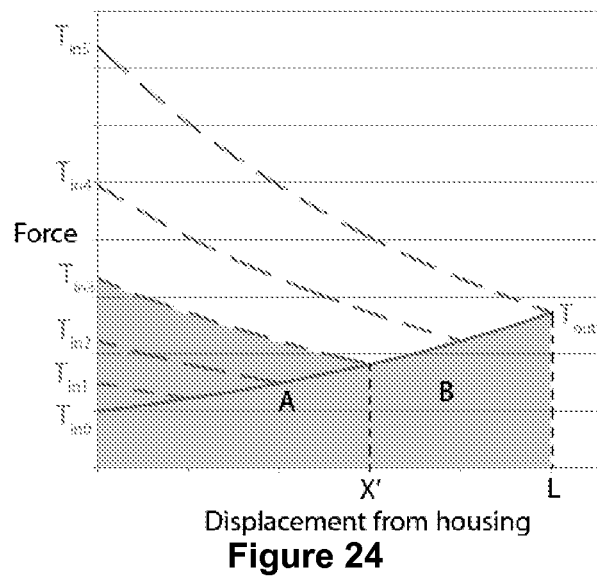
FIG. 24 is a graphical representation showing the gradually increasing $T_{in}$ and the tension distribution within the sheath.

With this equation found, the force at the end effector and elongation of the tendon and sheath are found for all the different phases when the system is used as shown in FIG. 24.

Experimental Setup

At the housing, or proximal end, two Faulhaber 2642W024CR DC servomotors with a gear head of 30/1S 134:1 ratio are placed. The two tendons, that are used to control one DOF, are fixed to the two actuators separately. These actuators are set to position control and each of them uses the rotary optical encoder HEDS-5540 A14 attached to the actuator to measure the angular rotation. The combined resolution of the encoder with the gear head is 67000 lines per revolution. At the end effector side, or distal end, another actuator is used under torque control. Its main purpose is to simulate the load that the end effector can apply to the environment. It also has the same rotary encoder attached to the actuator to measure the amount of movement made by the system. In the middle, two tendons and sheaths are used together with an overtube to prevent buckling. The forces at both ends of the system are measured with donut shaped load cells LW-1020 from Interface. Although they measure the compression experienced by the sheaths instead of the tension from the tendons, the result is similar to measuring the tension force at the same end, as shown in equation (2). The elastic modulus of the tendons must be known beforehand either from the supplier or measured with a simple stiffness test. The tendons used are Asahi 0.27 mm 7×7 Teflon coated wire rope with a length of approximately 2 m while the sheath is Acetone flat wire coil with outer diameter of 0.8 mm and inner diameter of 0.36 mm with a length of 2 m. The bending radius for the sheath and tendon is about 30 cm.

The rationale of using two actuators for a single DOF is to ensure only one tendon is providing a tension at a given time, while the antagonistic tendon is left loose. This provides the highest possible force from the tendon since it does not have to work against the other taut antagonistic tendon.

Necessary Steps for Prediction

Figure 25:
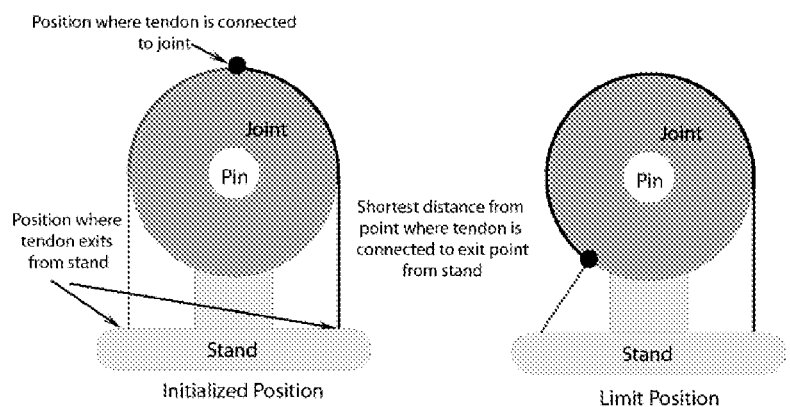
FIG. 25 is a simplified model showing the limit of motion for a simple revolute joint.

After the end effector reaches the site where it is designated to work, the global shapes of the tendon and sheath are fixed. The experimental procedure then goes as follows. First, it is necessary to determine the values of K and $M_e$ for this particular shape of the sheaths. To do so, initialization is required. The actuator at one end of the Degree of Freedom pulls one end of the tendon until the robotic manipulator reaches the end of its motion. This is the point where further pulling of the tendon at one side off the joint does not result in a change of the rotation angle, as shown in FIG. 25. Regarding the actuator at the other side of the degree of freedom, it must minimize the pulling force to prevent interference with the initialization procedure. This is possible since it is controlled by a separate actuator and it can read the load cell on its side, thus deciding either to pull or release the tendon accordingly.

Even when the joint at the distal end reaches the limit of its motion, the actuator on the pulling side can still continue to pull in the tendon at the proximal end. This length that is pulled can only come directly from the deformation of the tendon within the sheath. Using equation (11), $$M_e = \frac{e_{out}}{T_{in}},$$

$e_{out}$ is obtained from the encoder reading while $T_{in}$ is the force obtained from the load cell of the pulling side of at the proximal end. The value of $M_e$ can then be found from the process of initialization. Using equation (13), the value of K can be found using numerical method such as Newton Raphson. With these two values, the elongation and force at the distal end can be easily approximated since both elongation and force at the distal end is a simple function of $T_{in}$.

This is repeated for the opposite direction of the DOF as well to capture the specific value of $M_E$ and K. During initialization, the user has to ensure that the robotic manipulator does not touch any object or walls of the environment. After initialization, the user can start to use the MASTER as desired and the force at the end effector and elongation can be computed using the obtained K and $M_e$ value.

An assumption is made regarding the use of constants K and $M_e$. After the system has reached the site, the user no longer moves the system around and the shape of the sheaths can be assumed to be fixed. Only then can constants K and $M_e$ be used without producing much error. The user could always change the system position anytime, but the robotic system requires a quick initialization after every change.

The system is then tested by either torque control of the actuator at the distal end or allowing the distal end to push against a hard object or spring. The result when the robotic manipulator is pushing against a hard non-deformable object is shown in the following.

Figure 26:
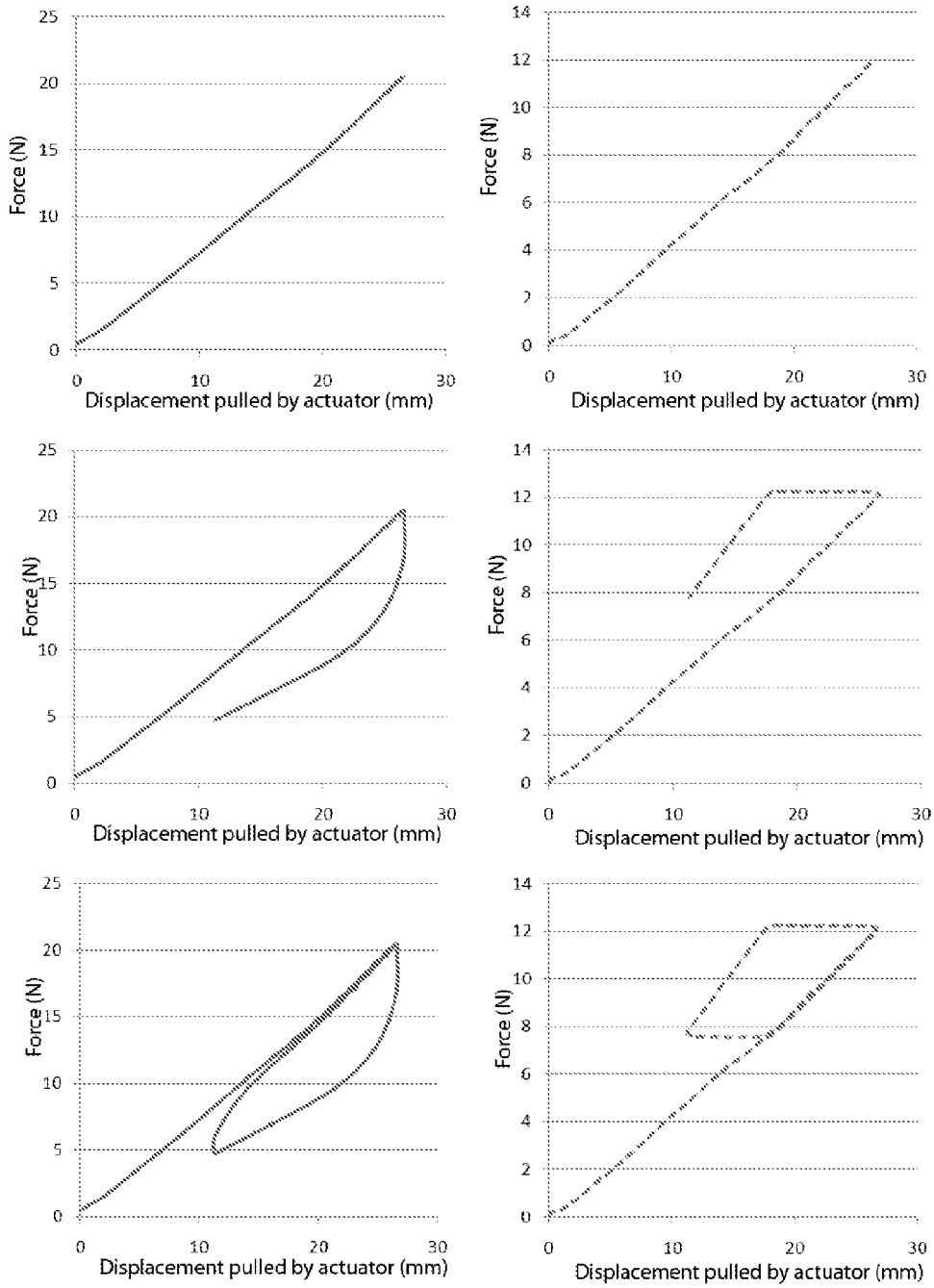
FIG. 26 is a graphical representation showing the phases of pulling and releasing that is studied.

First of all, the setup is initialized to obtain the K and $M_e$. The experiment is then performed with three profiles as seen in FIG. 26. In the first profile, the actuator pulls the tendon till it reaches a limited force of approximately 20N on the housing. In the second phase, the tendon is released at the housing to about 5N while in the third phase, the tendon is pulled again back to 20N. These last two phases test the pull-to-release, release, release-to-pull and pulling phases and check the approximation with the actual reading. In the figure, the curves on top are the readings from the housing load cell while the dotted curves below are the readings from the end effector load cell.

Figure 27:
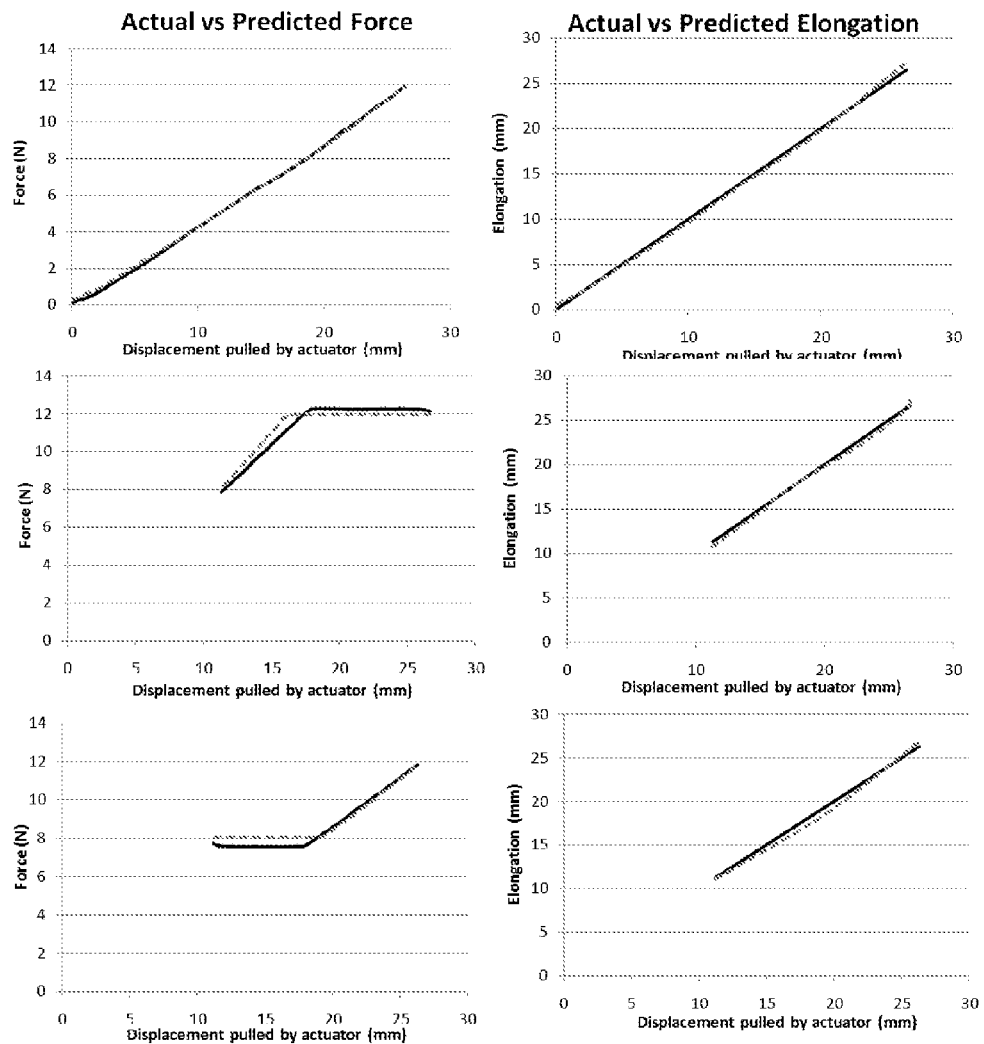
FIG. 27 is a graphical representation showing the result of the actual force/elongation vs predicted force/elongation.

The comparison of the end effector force with the predicted force is shown in FIG. 27. The results are broken up into three phases. The graphs on top are the plots of actual vs predicted end effector force while the graphs below are the actual vs predicted elongation plots. The continuous lines in full are the actual sensed values while the dotted lines are the predicted values. For this experiment, the maximum full scale error is approximately 7% while for the elongation, it is approximately 3%. The higher error in the force reading is due to the fact that the value of $M_e$ is found and then used to deduce K. Overall the average full scale error is less than 2%.

Although this method is capable of sensing both the elongation and end effector force, it could be applied only in cases whereby there is little or no change in the sheath shape after initialization. The greater the shape of the sheath changes, the worse the prediction becomes. If a great change of the shape of the sheath is suspected, it is recommended to reinitialize the system again to obtain updated values for $M_e$ and K. If the application force on the sheath undergoes regular displacements, then this method should not be used. However, if the application is not critical and does not require high accuracy, then small changes in the shape of the sheaths during usage can be tolerated.

The force predicted at the end effector is already the combined force the joint experienced. Therefore, it can directly be scaled to the controller without the need of any further calculation or conversion.

Whilst there has been described in the foregoing description preferred embodiments of the present invention, it will be understood by those skilled in the technology concerned that many variations in details of design, construction and/or operation may be made without departing from the present invention.

The invention claimed is:

1. A robotic manipulator for flexible endoscopy comprising:
    an arm;
    a flexible member comprising a tendon sheath system including a tendon in a sheath, the tendon deformable within the sheath such that the tendon and the sheath can exert forces upon and react against each other, the flexible member configured to be coupled to an endoscope, the flexible member having a first end and a second end, the first end of the flexible member connected to the arm such that the arm is movable by the flexible member, the second end of the flexible member couplable to an actuator to allow a physical movement of the arm to be controllable by a physical movement of a controller coupled to the actuator;
    an end effector connected to and movable by the arm; and
    an end effector force prediction unit configured to predict as a function of flexible member parameters sensed at the second end of the flexible member (a) tendon sheath system elongation including tendon elongation and sheath elongation at the first end of the flexible member and (b) force experienced by the end effector,
    wherein the end effector force prediction unit is configured to predict tendon sheath system elongation at the first end of the flexible member and force experienced by the end effector without requiring any sensor at a slave manipulator comprising the tendon, the arm, and the end effector.

2. The robotic manipulator according claim 1, wherein the tendon is an Ultra High Molecular Weight Polyethylene (UHMWPE) fibre and the sheath is a helical metal coil.

3. The robotic manipulator according to claim 1, wherein the arm is configured to have at least three of the following degrees of freedom:
    degree of freedom allowing forward and backward motion of the arm substantially parallel to a longitudinal axis of the endoscope;
    degree of freedom for controlling the opening and closing of the arm, the opening of the arm being a movement out of alignment with the longitudinal axis of the endoscope, and the closing of the arm being a movement to bring the arm into alignment with the longitudinal axis of the endoscope;
    degree of freedom for controlling the supination or pronation of the arm;
    degree of freedom for controlling the flexion or hyperextension of the arm; and
    optionally degree of freedom for controlling the opening and closing of the end effector of the arm.

4. The robotic manipulator according to claim 3, wherein each degree of freedom is controllable by two antagonistic tendons of the flexible member.

5. The robotic manipulator according to claim 4, wherein each antagonistic tendon is independently attachable to a corresponding actuator, and wherein each actuator is controlled by the controller.

6. The robotic manipulator according to claim 1, wherein the end effector is selected from the group consisting of a gripper, hook, pincer, forceps and knife.

7. The robotic manipulator according to claim 1, wherein the arm comprises a biosensor or a force sensor configured to provide a signal to the controller.

8. The robotic manipulator according to claim 1, wherein the end effector force prediction unit is configured for signal communication with the controller.

9. The robotic manipulator according to claim 1, wherein the end effector force prediction unit comprises:
    a set of sensors configured to sense information corresponding to the second end of the flexible member, wherein the information allows determination of specific parameters related to the tendon sheath system elongation at the first end of the flexible member and the force experienced by the end effector;
    a processor configured to analyse the parameters to determine a specific equation between (a) the force applied to the tendon sheath system at the second end of the flexible member and (b) the tendon sheath system elongation at the first end of the flexible member and the force experienced by the end effector; and
    a module configured to implement the equation at the controller.

10. The robotic manipulator according to claim 1, wherein the controller includes a movable hand-held member, and wherein the controller includes a microprocessor configured to:
    detect the motions of the hand-held member,
    scale the motion detected to suit the robotic manipulator, and
    transmit signals to the actuator for controlling the flexible member connected to the robotic manipulator.

11. The robotic manipulator according to claim 10, wherein the hand-held member includes a prime mover to receive signals to provide force feedback to a user using the hand-held member based upon the predicted force experienced by the end effector.

12. The robotic manipulator according to claim 10, wherein the hand-held member comprises grippers attachable to fingers of the user and all motion of the robotic manipulator is controllable using the grippers.

13. A method of treatment of a gastrointerinal tract related disease comprising the step of inserting the robotic manipulator of claim 1 into a natural orifice of the human body.

* * * * *